United States Patent
Wei et al.

(10) Patent No.: US 10,656,114 B2
(45) Date of Patent: May 19, 2020

(54) GAS SENSOR DEVICE INCLUDING GAS SENSORS AND SWITCHES, GAS SENSOR MODULE, AND GAS DETECTION METHOD

(71) Applicant: Panasonic Intellectual Property Management Co., Ltd., Osaka (JP)

(72) Inventors: Zhiqiang Wei, Osaka (JP); Kazunari Homma, Kyoto (JP); Koji Katayama, Nara (JP); Satoru Fujii, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 595 days.

(21) Appl. No.: 15/484,692

(22) Filed: Apr. 11, 2017

(65) Prior Publication Data

US 2017/0343507 A1 Nov. 30, 2017

(30) Foreign Application Priority Data

May 25, 2016 (JP) ................................ 2016-104539

(51) Int. Cl.
*G01N 27/414* (2006.01)
*G01N 33/00* (2006.01)
*G01N 27/12* (2006.01)

(52) U.S. Cl.
CPC ....... *G01N 27/4141* (2013.01); *G01N 27/122* (2013.01); *G01N 27/128* (2013.01); *G01N 33/005* (2013.01); *G01N 33/0031* (2013.01)

(58) Field of Classification Search
CPC ............. G01N 27/4141; G01N 27/122; G01N 27/128; G01N 33/0031; G01N 33/005

USPC ......................................................... 73/31.06
See application file for complete search history.

(56) References Cited

FOREIGN PATENT DOCUMENTS

| JP | 59-058348 | | 4/1984 |
|---|---|---|---|
| JP | 11-160267 | | 6/1999 |
| JP | 11160267 A | * | 6/1999 |
| JP | 2008-057976 | | 3/2008 |
| JP | 2015-125114 | | 7/2015 |

OTHER PUBLICATIONS

Song et al., "AlGaN/GaN Schottky diode hydrogen sensor performance at high temperatures with different catalytic metals"; Provided by Applicant (Year: 2005).*
Yu et al., "Hydrogen gas sensing properties of Pt/Ta2O5 Schottky diodes based on Si and SiC substrates" (Year: 2011).*

(Continued)

*Primary Examiner* — Nathaniel T Woodward
(74) *Attorney, Agent, or Firm* — McDermott Will & Emery LLP

(57) ABSTRACT

A gas sensor device includes gas sensors and switches. The switches are connected to the respective gas sensors in series. The gas sensors each include: a first conductive layer; a second conductive layer; a metal oxide layer disposed between the first conductive layer and the second conductive layer; and an insulation layer covering the first conductive layer, the second conductive layer, and the metal oxide layer and having an opening from which a portion of the second conductive layer is exposed. The resistance of the gas sensor is decreased when a gas containing a hydrogen atom comes into contact with the second conductive layer.

18 Claims, 17 Drawing Sheets

(56) References Cited

OTHER PUBLICATIONS

Translation of JP-11160267-A, Provided by Applicant (Year: 1999).*
J. Yu et al., "Hydrogen gas sensing properties of Pt/Ta2O5 Schottky diodes based on Si and SiC substrates", Sensors and Actuators A 172, pp. 9-14, Available online Feb. 25, 2011.

* cited by examiner

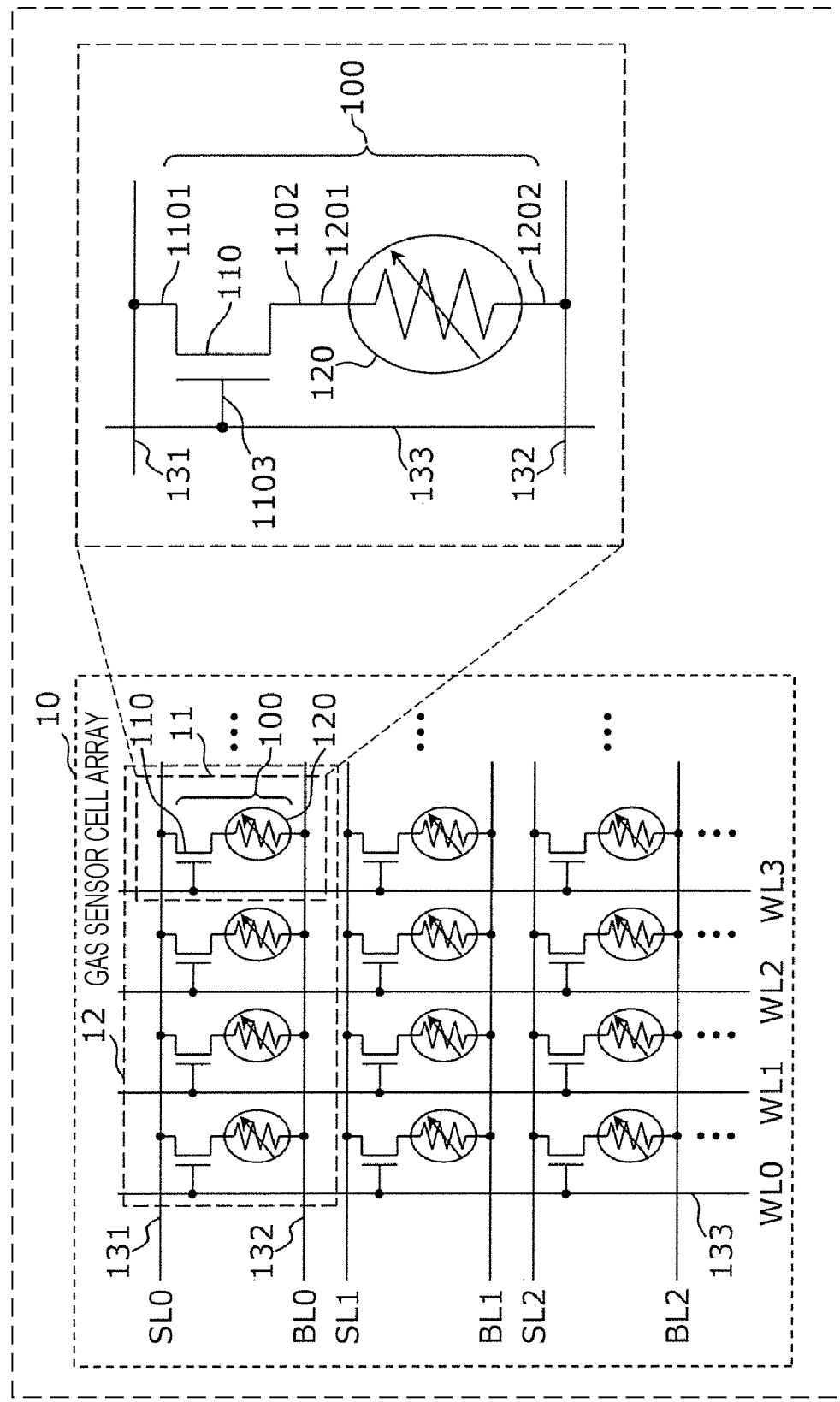

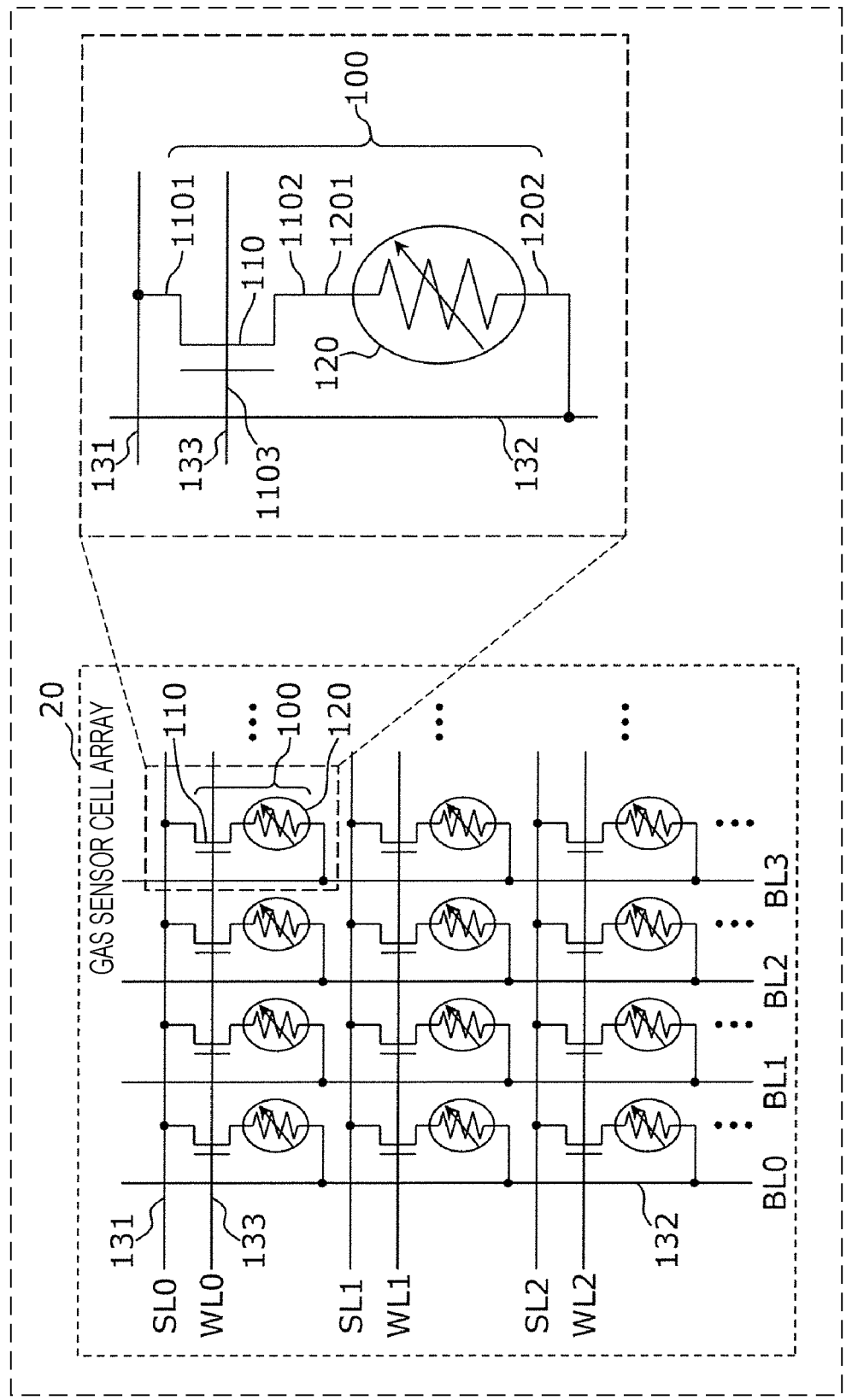

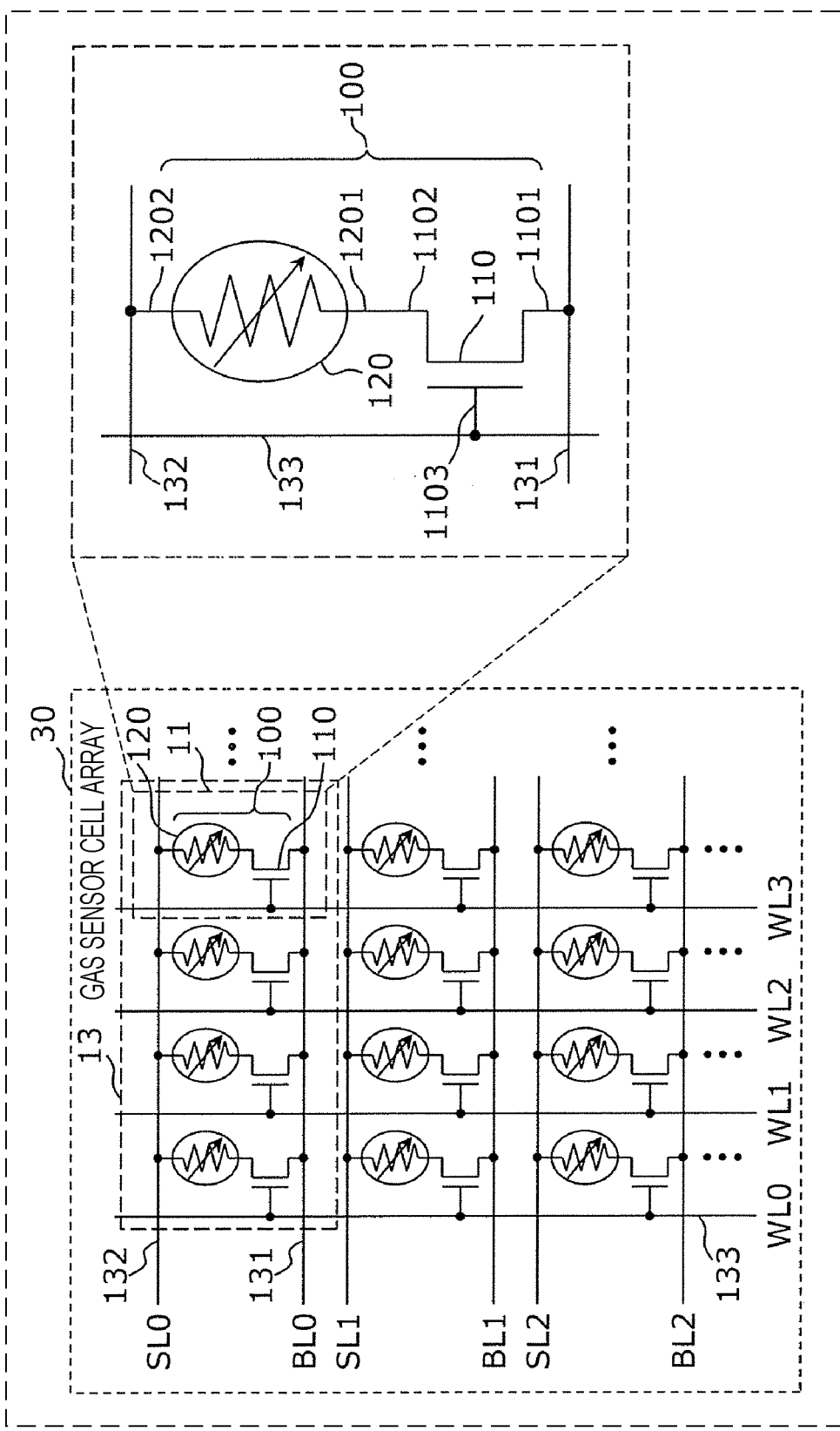

GAS SENSOR DEVICE INCLUDING GAS SENSORS AND SWITCHES, GAS SENSOR MODULE, AND GAS DETECTION METHOD

BACKGROUND

1. Technical Field

The present disclosure relates to a gas sensor device.

2. Description of the Related Art

Japanese Unexamined Patent Application Publication No. 59-58348 has disclosed a gas sensor which detects the presence of a hydrogen gas by the change in resistance. This gas sensor includes a material formed by adding palladium (Pd) and a glass to tantalum pentoxide ($Ta_2O_5$) and platinum (Pt) electrodes sandwiching the material.

In Sensors and Actuators A 172 (2011), p. 9-14, a Pt/$Ta_2O_5$ Schottky diode for hydrogen sensing has been disclosed. In this Schottky diode, a hydrogen molecule is dissociated into hydrogen atoms on the surface of a Pt catalyst.

SUMMARY

In one general aspect, the techniques disclosed here feature a gas sensor device which comprises gas sensors and switches. The switches are connected to the respective gas sensors in series. The gas sensors each include: a first conductive layer; a second conductive layer; a metal oxide layer disposed between the first conductive layer and the second conductive layer, the metal oxide layer including a bulk region and a local region surrounded by the bulk region, a degree of oxygen deficiency of the local region being higher than that of the bulk region; and an insulation layer covering the first conductive layer, the second conductive layer, and the metal oxide layer, the insulation layer having an opening from which a portion of the second conductive layer is exposed. The resistances of the gas sensors are each decreased when a gas containing a hydrogen atom is brought into contact with the second conductive layer.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 1A is an equivalent circuit diagram showing one example of a gas sensor cell array according to a first embodiment;

FIG. 1B is an equivalent circuit diagram showing one example of the gas sensor cell array according to the first embodiment;

FIG. 1C is an equivalent circuit diagram showing one example of the gas sensor cell array according to the first embodiment;

DETAILED DESCRIPTION

Figure 2:
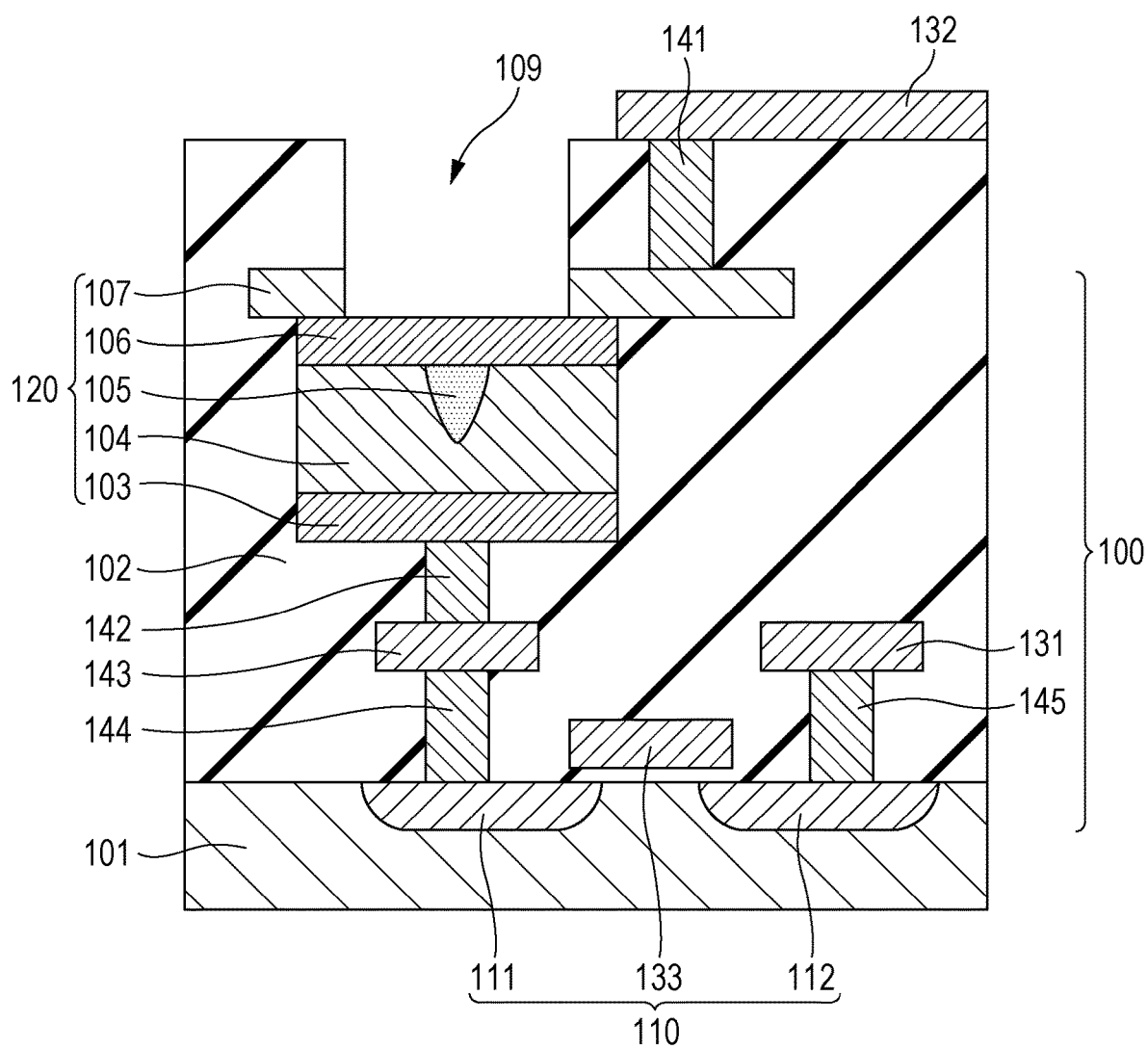
FIG. 2 is a cross-sectional view sowing one example of a gas sensor cell according to the first embodiment.

Underlying Knowledge Forming Basis of the Present Disclosure

Through intensive research carried out by the present inventors, in a related gas sensor, the following problems were discovered. In a related gas sensor, in order to improve the sensitivity to detect a gas having a hydrogen atom, a gas detection element is heated to 100° C. or more. Hence, the power consumption of a related gas sensor is at least approximately 100 mW. Accordingly, when a gas sensor is always used in an ON state, a problem in that the power consumption is remarkably increased may arise.

In order to solve the problem described above, the present inventors found a novel gas sensor element. This gas sensor element includes a first conductive layer, a second conductive layer, a metal oxide layer, a local region, and an insulation layer. The first conductive layer and the second conductive layer are disposed so that the principal surfaces thereof face each other. The metal oxide layer is disposed in contact with the principal surface of the first conductive layer and the principal surface of the second conductive layer. The local region is disposed in the metal oxide layer in contact with the second conductive layer and has a high degree of oxygen deficiency as compared to that of the metal oxide layer. The insulation layer covers the first conductive layer, the second conductive layer, and the metal oxide layer, and at least a portion of the other surface of the second conductive layer facing the principal surface thereof is exposed without being covered with the insulation layer.

According to this gas sensor element, for example, without performing heating by a heater, a hydrogen-containing gas can be detected with a small power consumption.

While the electrical power saving of this gas sensor element is used, the present inventors investigated a gas sensor capable of improving a detection sensitivity. As a result, the present inventors conceived the following gas sensor.

Hereinafter, embodiments of the present disclosure will be described with reference to the drawings.

Incidentally, in the drawings, an element having substantially the same structure, operation, and effect as that described already will be designated by the same reference numeral, and the description thereof will be omitted. In addition, the numerical value, the material, the composition, the shape, the film forming method, the arrangement of constituent elements, the connection therebetween, and the like, which will be described below, are shown by way of example in order to particularly explain the embodiment of the present disclosure, and the present disclosure is not limited thereto. In addition, among the constituent elements of the following embodiments, the constituent element which is not described in the independent claim representing the most generic concept will be described as an arbitrary constituent element.

First Embodiment

FIG. 1A is an equivalent circuit diagram of a gas sensor cell array forming an important portion of a gas sensor according to a first embodiment.

As shown in FIG. 1A, a gas sensor cell array 10 includes gas sensor cells 100, first wires 131, second wires 132, and third wires 133. The gas sensor cells 100, the first wires 131, the second wires 132, and the third wires 133 may be disposed on a single substrate.

In each of the gas sensor cells 100, a selection element 110 in which a conductive state and a non-conductive state can be switched therebetween is connected in series to a gas sensor element 120 having a resistance which is decreased in response to a gas containing a gas molecule having a hydrogen atom. The gas sensor cells 100 are electrically connected to each other with the first wires 131, the second wires 132, and the third wires 133 interposed therebetween.

The selection element 110 includes a first terminal 1101, a second terminal 1102, and a control terminal 1103, and in response to an electrical signal to be applied to the control terminal 1103, the conductive state and the non-conductive state between the first terminal 1101 and the second terminal 1102 are switched therebetween. The selection element 110 may be formed, for example, of an NMOS transistor, and in this case, the first terminal 1101 and the second terminal 1102 correspond to a source and a drain electrode, and the control terminal 1103 corresponds to a gate electrode.

The gas sensor element 120 has a first terminal 1201 and a second terminal 1202, and in response to a gas containing a molecule having a hydrogen atom, the resistance between the first terminal 1201 and the second terminal 1202 is decreased. Details of the gas sensor element 120 will be described later.

The gas sensor cell 100 is formed by connecting the second terminal 1102 of the selection element 110 to the first terminal 1201 of the gas sensor element 120, that is, by connecting the selection element 110 to the gas sensor element 120 in series.

The gas sensor cells 100 may be electrically connected to each other so that in at least one arbitrarily selected gas sensor cell 100, a predetermined operation can be executed, and a concrete connection mode is not particularly limited. In the predetermined operation described above, a sensing operation of a resistive state of the gas sensor element 120 is included, and a setting operation of the resistive state thereof may also be included.

For example, as shown in FIG. 1A, in the gas sensor cell array 10, the gas sensor cells 100 may be arranged in a matrix form, the first wires 131 and the second wires 132 may be provided along the respective lines, and the third wires 133 may be provided along the respective rows. The first terminal 1101 of the selection element 110 and the second terminal 1202 of the gas sensor element 120 are connected to the first wire 131 and the second wire 132, respectively, provided along the lines at which the gas sensor cell 100 is disposed. In addition, the control terminal 1103 of the selection element 110 is connected to the third wire 133 provided along the row at which the gas sensor cell 100 is disposed.

The first wire 131, the second wire 132, and the third wire 133 correspond to a source line SLi (i=0, 1, 2, - - - ), a bit line BLi (i=0, 1, 2, - - - ), and a word line WLj (j=0, 1, 2, 3 - - - ), respectively.

According to the gas sensor cell array 10 formed as described above, while an operation voltage is simultaneously applied to gas sensor cells 100 on a desired line through a source line and a bit line, selection elements 110 on a desired row can be controlled in the conductive state through a word line. Accordingly, at least one gas sensor cell 100 (for example, only one gas sensor cell located at a specific matrix position) selected from the gas sensor cells 100 can be operated.

In addition, the structure in which the gas sensor cells 100 are connected to each other is not limited to the example shown in FIG. 1A.

FIG. 1B is another equivalent circuit diagram of the gas sensor according to the first embodiment. As shown in FIG. 1B, in a gas sensor cell array 20, the gas sensor cells 100 are arranged in a matrix form, the first wires 131 and the third wires 133 may be provided along the respective lines, and the second wires 132 may be provided along the respective rows. The first terminal 1101 of the selection element 110 is connected to the first wire 131 provided along the line at which the gas sensor cell 100 is disposed. The second terminal 1202 of the gas sensor element 120 is connected to the second wire 132 provided along the row at which the gas sensor cell 100 is disposed. In addition, the control terminal 1103 of the selection element 110 is connected to the third wire 133 provided along the line at which the gas sensor cell 100 is disposed.

The first wire 131, the second wire 132, and the third wire 133 correspond to a source line SLi (i=0, 1, 2, - - - ), a bit line BLj (j=0, 1, 2, 3 - - - ), and a word line WLi (i=0, 1, 2, - - - ), respectively.

According to the gas sensor cell array 20 formed as described above, while an operation voltage is applied to a gas sensor cell 100 located at a specific matrix position through a source line and a bit line, selection elements 110 can also be controlled in the conductive state through a word line. Accordingly, at least one gas sensor cell 100 (for example, only one gas sensor cell located at a specific matrix position) selected from the gas sensor cells 100 can be operated.

FIG. 1C is another equivalent circuit diagram of the gas sensor according to the first embodiment. As shown in FIG. 1C, in a gas sensor cell array 30, the gas sensor cells 100 are arranged in a matrix form, the first wires 131 and the second wires 132 may be provided along the respective lines, and the third wires 132 may be provided along the respective rows. The first terminal 1101 of the selection element 110 and the second terminal 1202 of the gas sensor element 120 are connected to the first wire 131 and the second wire 132, respectively, provided along the lines at which the gas sensor cell 100 is disposed. In addition, the control terminal 1103 of the selection element 110 is connected to the third wire 133 provided along the row at which the gas sensor cell 100 is disposed.

The first wire 131, the second wire 132, and the third wire 133 correspond to a bit line BLi (i=0, 1, 2, - - - ), a source line SLi (i=0, 1, 2, - - - ), and a word line WLj (j=0, 1, 2, 3 - - - ), respectively.

According to the gas sensor cell array 30 formed as described above, while an operation voltage is applied to gas sensor cells 100 on a desired line through a source line and a bit line, selection elements 110 can also be controlled in the conductive state through a word line. Accordingly, at least one gas sensor cell 100 (for example, only one gas sensor cell located at a specific matrix position) selected from the gas sensor cells 100 can be operated.

According to the gas sensor cell arrays 10, 20, and 30, for example, under the control of an exterior control circuit, while at least one gas sensor cell 100 is sequentially selected, a setting operation and a sensing operation of the resistive state can be performed on the selected gas sensor cell 100. As a result, without instantaneously consuming a large operation electrical power, the setting operation and the sensing operation of the resistive state can be performed on all the gas sensor cells 100, and hence, a gas sensor cell array suitable to simultaneously achieve a low power consumption and a high sensitivity can be obtained.

Next, the structure of the gas sensor cell will be described.

FIG. 2 is a cross-sectional view showing a portion including the gas sensor cell 100 of the gas sensor cell array 10. FIG. 2 is one example of a cross-sectional structure of a portion 11 shown in FIG. 1A and shows electrical conductors forming various types of wires together with the gas sensor cell 100. The gas sensor cell 100 is formed, in particular, of a transistor used as the selection element 110 formed on a substrate 101 and the gas sensor element 120 formed above the substrate 101.

The portion 11 of the gas sensor cell array 10 includes the substrate 101, an insulation layer 102, a first conductive layer 103, a resistive film 104, a local region 105, a second conductive layer 106, a third conductive layer 107, a source region 111, a drain region 112, the first wire 131, the second wire 132, the third wire 133, vias 141 and 142, a lower wire 143, and contact plugs 144 and 145. In this case, the resistive film 104 is one example of a metal oxide layer.

In the substrate 101, the source region 111 and the drain region 112 are formed. For example, the source region 111 and the drain region 112 each may be an N$^+$ diffusion region. The third wire 133 is disposed between the source region 111 and the drain region 112 and above the substrate 101 with an oxide insulation film (not shown) interposed therebetween. By the source region 111, the drain region 112, and the third wire 133 functioning as a gate electrode, an N-type MOS transistor is formed as the selection element 110. A ground potential is applied to the substrate 101.

The third wire 133 may be formed, for example, of a polysilicon. In addition, although the substrate 101 may be formed, for example, of a single crystal silicon substrate or a semiconductor substrate, the substrate 101 is not limited thereto. Since the resistive film 104 can be formed at a relatively low substrate temperature, for example, the resistive film 104 may also be formed on a flexible substrate formed from a resin material. In the case of a flexible substrate, the selection element 110 is formed of a thin film transistor (TFT).

The insulation layer 102 is disposed on the substrate 101, and the first conductive layer 103, the resistive film 104, the local region 105, the second conductive layer 106, the third conductive layer 107, the first wire 131, the third wire 133, the vias 141 and 142, the lower wire 143, and the contact plugs 144 and 145 are covered with the insulation layer 102.

The first conductive layer 103 and the second conductive layer 106 are disposed so that the respective principal surfaces thereof face each other. The resistive film 104 is disposed in contact with the principal surface of the first conductive layer 103 and the principal surface of the second conductive layer 106.

In the insulation layer 102 and the third conductive layer 107, an opening 109 is provided so that a gas to be inspected is brought into contact with the second conductive layer 106. In other words, while the insulation layer 102 covers the first conductive layer 103, the second conductive layer 106, the third conductive layer 107, and the resistive film 104, at least a portion of the upper surface (the other surface facing the principal surface described above) of the second conductive layer 106 is exposed without being covered with the insulation layer 102 and the third conductive layer 107.

By a laminate including the first conductive layer 103, the resistive film 104, the local region 105, the second conductive layer 106, and the third conductive layer 107, the gas sensor element 120 is formed.

The second conductive layer 106 may be formed, for example, of a material, such as platinum or palladium, having a catalyst function. The third electrically conductive layer 107 may be formed, for example, of an conductive material, such as titanium nitride (TiN).

The resistive film 104 is provided between the first conductive layer 103 and the second conductive layer 106. The resistance of the resistive film 104 is reversibly changed in accordance with an electrical signal applied between the first conductive layer 103 and the second conductive layer 106. In particular, the resistive state of the resistive film 104 is reversibly changed between a high resistive state and a low resistive state in accordance with a voltage (potential difference) applied between the first conductive layer 103 and the second conductive layer 106. In addition, the resistive state of the resistive film 104 is changed from a high resistive state to a low resistive state in response to a hydrogen-containing gas which is brought into contact with the second conductive layer 106.

The local region 105 is formed from the same metal oxide as that of the resistive film 104 and is disposed in the resistive film 104 so as to be in contact with the second conductive layer 106 and to be not in contact with the first conductive layer 103. The degree of oxygen deficiency of the local region 105 is high as compared to the degree of oxygen deficiency of the periphery thereof (that is, a bulk region of the resistive film 104). The degree of oxygen deficiency of the local region 105 is reversibly changed in accordance with an electrical signal to be applied between the first conductive layer 103 and the second conductive layer 106. In addition, the local region 105 is changed from the state of a low degree of oxygen deficiency to the state of a high degree of oxygen deficiency in response to a hydrogen-containing gas which is brought into contact with the second conductive layer 106.

The local region 105 is a minute region in which a filament (conductive path) formed from oxygen defect sites is assumed to be generated and lost. A resistance change phenomenon in the resistive film 104 is believed a phenomenon in which the change in resistance occurs when the filament is generated or lost by an oxidation-reduction reaction performed in the local region 105.

In addition, in the present disclosure, the "degree of oxygen deficiency" of a metal oxide indicates the rate of a deficient amount of oxygen of the metal oxide to the amount of oxygen of an oxide having a stoichiometric composition formed from the same elements as those of the metal oxide (in this case, the deficient amount of oxygen is obtained by deducting the amount of oxygen of the metal oxide from the amount of oxygen of a metal oxide having a stoichiometric composition). If there are a plurality of metal oxides having stoichiometric compositions formed from the same elements as those of the metal oxide, the degree of oxygen deficiency of the metal oxide is defined by one metal oxide having the highest resistance among the metal oxides having stoichiometric compositions. A metal oxide having a stoichiometric composition is stabler than a metal oxide having another composition and has a higher resistance than that thereof.

For example, when the metal is tantalum (Ta), since an oxide having a stoichiometric composition by the above definition is $Ta_2O_5$, it can be represented by $TaO_{2.5}$. The degree of oxygen deficiency of $TaO_{2.5}$ is 0%, and the degree of oxygen deficiency of $TaO_{1.5}$ is (2.5-1.5)/2.5=40%. In addition, a metal oxide having an excess amount of oxygen has a negative degree of oxygen deficiency. In addition, in the present disclosure, unless otherwise particularly noted, the degree of oxygen deficiency can be represented by a positive value, 0, or a negative value.

An oxide having a low degree of oxygen deficiency has a high resistance since being closer to an oxide having a stoichiometric composition, and an oxide having a high degree of oxygen deficiency has a low resistance since being closer to a metal forming the oxide.

An "oxygen content" is the rate of the number of oxygen atoms to the total number of atoms. For example, the oxygen content of $Ta_2O_5$ is a rate (O/(Ta+O)) of the number of oxygen atoms to the total number of atoms and is 71.4 atomic percent. Hence, the oxygen content of an oxygen deficient-type tantalum oxide is larger than 0 and smaller than 71.4 atomic percent.

The local region 105 is formed in the resistive film 104 by applying an initial break voltage between the first conductive layer 103 and the second conductive layer 106. In other words, the initial break voltage is a voltage to be applied between the first conductive layer 103 and the second conductive layer 106 in order to form the local region 105. The absolute value of the initial break voltage may be higher than a writing voltage. The writing voltage is a voltage to be applied between the first conductive layer 103 and the second conductive layer 106 so that the resistive film 104 is reversibly changed between a high resistive state and a low resistive state. Alternatively, the absolute value of the initial break voltage may be lower than the above setting voltage. In this case, the initial break voltage may be repeatedly applied or may be continuously applied for a predetermined time. By application of the initial break voltage, as shown in FIG. 2, the local region 105 in contact with the second conductive layer 106 and not in contact with the first conductive layer 103 is formed.

The local region 105 is a minute region corresponding to filaments required for a current flow. The formation of filaments in the local region 105 may be explained using a percolation model.

The percolation model is a model based on the theory in which a random distribution of oxygen defect sites in the local region 105 is assumed, and when the density of the oxygen defects sites or the like exceeds a predetermined threshold value, the probability of forming linkage between the oxygen defect sites is increased.

According to the percolation model, the filament is formed when a plurality of oxygen defect sites in the local region 105 are linked with each other, and the change in resistance of the resistive film 104 occurs when the oxygen defect sites in the local region 105 are generated and lost.

In this embodiment, the "oxygen defect" indicates that oxygen in this metal oxide is deficient from the stoichiometric composition thereof, and the "density of oxygen defect sites" also corresponds to the degree of oxygen deficiency. That is, when the degree of oxygen deficiency is increased, the density of oxygen defect sites is also increased.

The local region 105 may be formed only at one place of the resistive film 104 of the gas sensor cell 100. The number of local regions 105 formed in the resistive film 104 may be confirmed, for example, by an electron beam absorbed current (EBAC) analysis.

When the local region 105 is present in the resistive film 104, by application of a voltage between the first conductive layer 103 and the second conductive layer 106, a current in the resistive film 104 flows concentratedly through the local region 105.

The size of the local region 105 is small. Hence, for example, the local region 105 generates heat by a current of approximately several tens of microamperes which flows when the resistance is read, and by this heat generation, a significant increase in temperature occurs. When a current of approximately several tens of microamperes flows, the power consumption thereby is less than 0.1 mW.

The second conductive layer 106 is formed of a metal (such as Pt) having a catalyst function, and the local region 105 is in contact with the second conductive layer 106. By the structure as described above, the second conductive layer 106 is heated by the heat generation in the local region 105, and a hydrogen atom is efficiently dissociated from a hydrogen-containing gas.

When a hydrogen-containing gas is contained in a gas to be inspected, at the second conductive layer 106, a hydrogen atom is dissociated from a hydrogen-containing gas, the hydrogen atom thus dissociated is bonded to an oxygen atom in the local region 105, and as a result, the resistance of the local region 105 is decreased.

As described above, the gas sensor element 120 has a characteristic in which the resistance between the first conductive layer 103 and the second conductive layer 106 is decreased when the second conductive layer 106 is in contact with a hydrogen-containing gas, that is, the gas sensor element 120 has a gas sensitivity. By this characteristic described above, when a gas to be inspected is brought into contact with the second conductive layer 106, by detecting the decrease in resistance between the first conductive layer 103 and the second conductive layer 106, a hydrogen-containing gas contained in the gas can be detected. The characteristic described above can be activated by the heat generation in the local region 105.

In addition, even if the local region 105 is placed in any one of a high resistive state and a low resistive state, when a hydrogen-containing gas is brought into contact with the second conductive layer 106, the resistance is further decreased. Hence, regardless of whether the local region 105 is placed in any one of a high resistive state and a low resistive state, the gas sensor element 120 can detect a hydrogen-containing gas. However, in order to more clearly detect the decrease in resistance, a gas sensor element 120 in which the local region 105 is set in a high resistive state in advance may also be used.

Next, the operation of setting the resistive state of the gas sensor element 120 by voltage application will be described.

Figure 3:
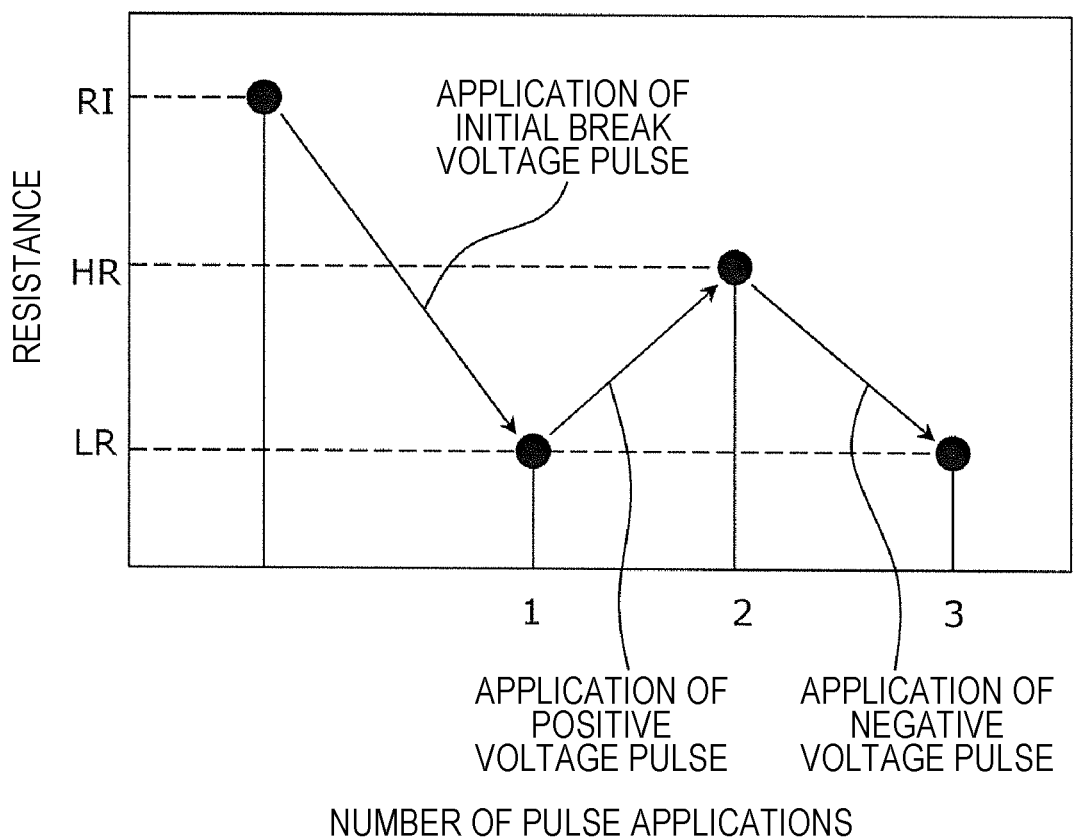
FIG. 3 is a graph showing one example of a resistance change characteristic of a gas sensor element according to the first embodiment by voltage application.

FIG. 3 is a graph showing a resistance change characteristic of the gas sensor element 120 by voltage application. FIG. 3 shows one example of the resistance change when an initial break voltage pulse, a positive voltage pulse, and a negative voltage pulse are applied to the gas sensor element 120.

As shown in FIG. 3, when the resistance of the gas sensor element 120 is an initial resistance RI (higher than a resistance HR in a high resistive state), the initial break voltage is applied between the first conductive layer 103 and the second conductive layer 106. As a result, the local region 105 is formed, and the resistance is decreased. Subsequently, when the positive voltage pulse and the negative voltage pulse are alternately applied between the first conductive layer 103 and the second conductive layer 106 of the gas sensor element 120, the resistance of the resistive film 104 is reversibly changed. The positive voltage pulse and the negative voltage pulse may be voltage pulses, for example, having an amplitude equal to or more than a predetermined threshold capable of changing the resistive state of the gas sensor element 120, a pulse width of 100 ns, and polarities different from each other. The positive voltage pulse and the negative voltage pulse are each one example of the setting voltage.

In particular, as the setting voltage, when a positive voltage pulse is applied between the first conductive layer 103 and the second conductive layer 106, the resistance of the resistive film 104 is increased from a low resistance LR to a high resistance HR. On the other hand, as the setting voltage, when a negative voltage pulse is applied between the conductive layers, the resistance of the resistive film 104 is decreased from the high resistance HR to the low resistance LR. In addition, as for the polarity of the voltage pulse, when the potential of the second conductive layer 106 is high as compared to that of the first conductive layer 103, the polarity is "positive", and when the potential of the second conductive layer 106 is low as compared to that of the first conductive layer 103, the polarity is "negative".

By the use of the resistance change characteristic obtained by the voltage application as described above, before monitoring of a hydrogen-containing gas is started, when a positive voltage pulse is applied between the first conductive layer 103 and the second conductive layer 106, a hydrogen-containing gas can be detected using the gas sensor cell 100 which is set in the high resistive state (HR). Accordingly, compared to the case in which a hydrogen-containing gas is detected using the gas sensor cell 100 which is set in the low resistive state (LR), the decrease in resistance can be more clearly detected; hence, a detection performance of a hydrogen-containing gas is improved.

In addition, when the resistance of the gas sensor element 120 is read, a voltage pulse having a small amplitude which does not change the resistive state of the resistive film 104 is applied to the gas sensor element 120, and a current flowing in the gas sensor element 120 is measured. The amplitude of the voltage pulse described above is smaller than that of the setting voltage. The voltage pulse having a small amplitude is one example of the sensing voltage.

Next, details of the gas sensor element 120 configured to obtain a stable resistance change characteristic will be described.

The resistive film 104 is formed of an oxygen deficient-type metal oxide. A mother metal of the metal oxide may be at least one selected from the group consisting of transition metals, such as tantalum (Ta), hafnium (Hf), titanium (Ti), zirconium (Zr), niobium (Nb), tungsten (W), nickel (Ni), and iron (Fe), and aluminum (Al). Since a transition metal is able to have a plurality of oxidized states, different resistive states can be realized by an oxidation-reduction reaction. In this case, the oxygen deficient-type metal oxide is a metal oxide having a high degree of oxygen deficiency as compared to a metal oxide which contains the same metal as that thereof and which has a stoichiometric composition. A metal oxide having a stoichiometric composition is a typical insulation material, and on the other hand, an oxygen deficient-type metal oxide typically shows semiconductor characteristics. When an oxygen deficient-type metal oxide is used for the resistive film 104, the gas sensor element 120 is able to realize a stable resistance change operation with good reproducibility.

For example, when a hafnium oxide is used as a metal oxide forming the resistive film 104, and the composition thereof is represented by $HfO_x$, if x is 1.6 or more, the resistance of the resistive film 104 can be stably changed. In this case, the thickness of the hafnium oxide may be set to 3 to 4 nm.

In addition, when a zirconium oxide is used as a metal oxide forming the resistive film 104, and the composition thereof is represented by $ZrO_x$, if x is 1.4 or more, the resistance of the resistive film 104 can be stably changed. In this case, the thickness of the zirconium oxide may be set to 1 to 5 nm.

In addition, when a tantalum oxide is used as a metal oxide forming the resistive film 104, and the composition thereof is represented by $TaO_x$, if x is 2.1 or more, the resistance of the resistive film 104 can be stably changed.

The compositions of the above respective metal oxide layers each can be measured using a Rutherford backscattering method.

As a material of the first conductive layer 103 and the second conductive layer 106, for example, one selected from the group consisting of platinum (Pt), iridium (Ir), palladium (Pd), silver (Ag), nickel (Ni), tungsten (W), copper (Cu), aluminum (Al), tantalum (Ta), titanium (Ti), titanium nitride (TiN), tantalum nitride (TaN), and titanium aluminum nitride (TiAlN) may be used.

In particular, the second conductive layer 106 may be formed, for example, of a material having a catalyst function, such as platinum (Pt), iridium (Ir), or palladium (Pd), which dissociates a hydrogen atom from a gas molecule having a hydrogen atom. In addition, the first conductive layer 103 may be formed, for example, of a material having a low standard electrode potential, such as tungsten (W), nickel (Ni), tantalum (Ta), titanium (Ti), aluminum (Al), tantalum nitride (TaN), or titanium nitride (TiN), as compared to that of a metal forming the metal oxide. As the standard electrode potential of a metal is higher, the metal is more unlikely to be oxidized.

In addition, the resistive film is not limited to a single-layer resistive film 104 and may be formed of a laminate of a first metal oxide layer and a second metal oxide layer.

Figure 4:
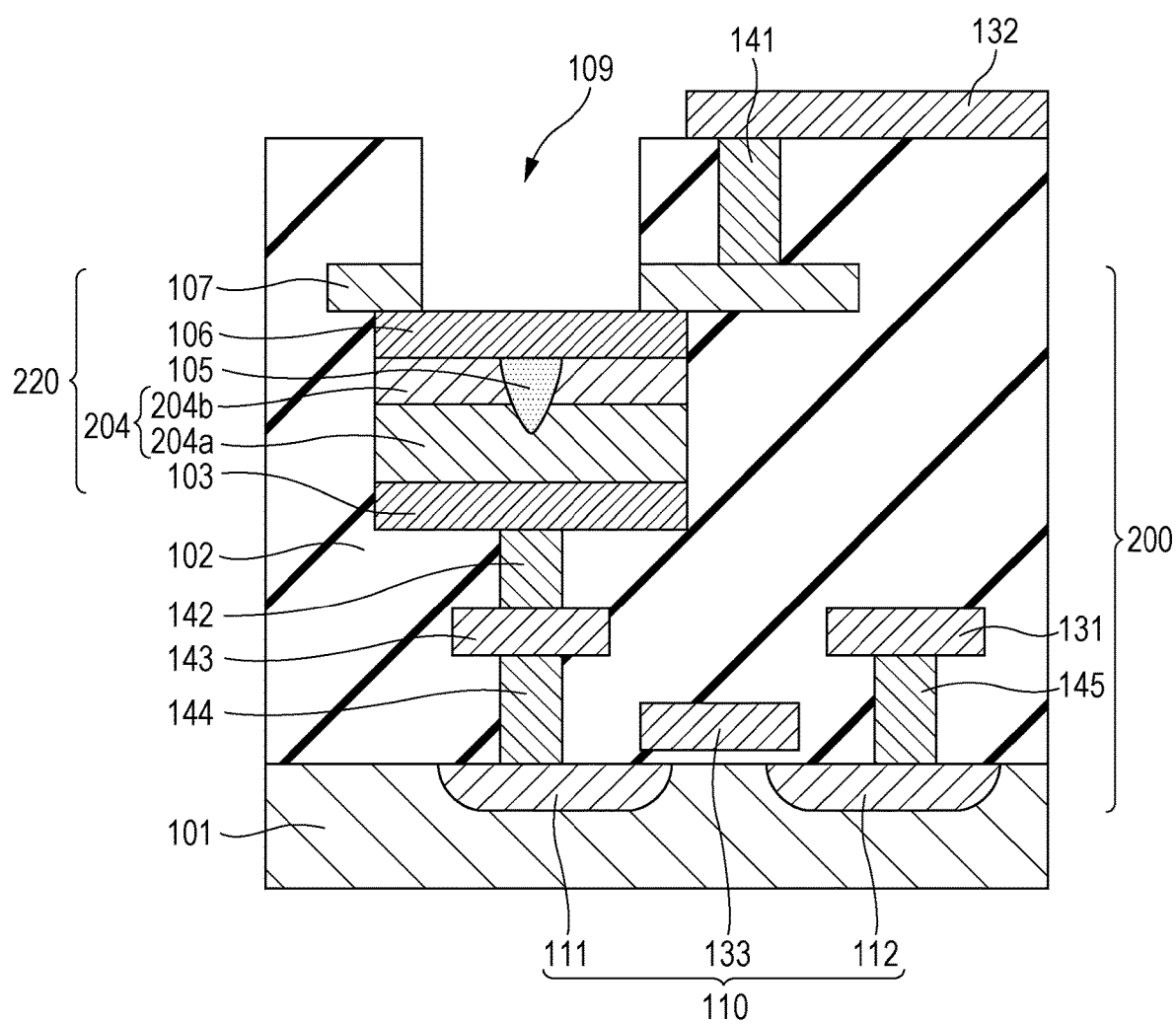
FIG. 4 is a cross-sectional view showing a gas sensor cell according to a modified example of the first embodiment.

FIG. 4 is a cross-sectional view of a gas sensor cell according to a modified example of the first embodiment. FIG. 4 shows one example of a cross-sectional structure of the portion 11 shown in FIG. 1A, and a gas sensor element 220 of a gas sensor cell 200 is changed from that shown in FIG. 2.

The gas sensor element 220 is different from the gas sensor element 120 since a resistive film 204 is formed by laminating two layers, that is, a first metal oxide layer 204a in contact with the first conductive layer 103 and a second metal oxide layer 204b in contact with the second conductive layer 106. In addition, the resistive film 204 may be formed by laminating not only two but also at least three metal oxide layers.

In the first metal oxide layer 204a and the second metal oxide layer 204b, the local region 105 is provided in which the degree of oxygen deficiency is reversibly changed in response to the application of an electrical pulse and a hydrogen-containing gas. The local region 105 is formed to penetrate at least the second metal oxide layer 204b and to be in contact with the second conductive layer 106.

In other words, the resistive film 204 has a laminate structure at least including the first metal oxide layer 204a containing a first metal oxide and the second metal oxide layer 204b containing a second metal oxide. In addition, the first metal oxide layer 204a is disposed between the first conductive layer 103 and the second metal oxide layer 204b, and the second metal oxide layer 204b is disposed between the first metal oxide layer 204a and the second conductive layer 106.

The thickness of the second metal oxide layer 204b may be smaller than that of the first metal oxide layer 204a. In this case, the local region 105 can be easily formed so as not to be in contact with the first conductive layer 103. The degree of oxygen deficiency of the second metal oxide layer 204b may be low as compared to that of the first metal oxide layer 204a. In this case, since the resistance of the second metal oxide layer 204b is higher than that of the first metal oxide layer 204a, the voltage applied to the resistive film 204 is mostly applied to the second metal oxide layer 204b. By the structure described above, for example, the initial break voltage can be concentrated to the second metal oxide layer 204b, and hence, the initial break voltage required to form the local region 105 can be effectively decreased.

In addition, in the present disclosure, when the metal forming the first metal oxide layer 204a is the same as that forming the second metal oxide layer 204b, instead of using the "degree of oxygen deficiency", the term "oxygen content" may be used in some cases. The "high oxygen content" corresponds to the "low degree of oxygen deficiency", and the "low oxygen content" corresponds to the "high degree of oxygen deficiency".

However, the resistive film 204 according to this embodiment is not limited to the case in which the metal forming the first metal oxide layer 204a is the same as that forming the second metal oxide layer 204b, and the metal of the metal oxide layer 204a may be different from the metal of the second metal oxide layer 204b. That is, the first metal oxide layer 204a and the second metal oxide layer 204b may be formed from oxides containing different metals from each other.

When a first metal forming the first metal oxide layer 204a is the same as a second metal forming the second metal oxide layer 204b, the oxygen content inversely corresponds to the degree of oxygen deficiency. That is, when the oxygen content of the second metal oxide is higher than that of the first metal oxide, the degree of oxygen deficiency of the second metal oxide is lower than that of the first metal oxide.

The resistive film 204 includes the local region 105 in the vicinity of the interface between the first metal oxide layer 204a and the second metal oxide layer 204b. The degree of oxygen deficiency of the local region 105 is high as compared to that in the vicinity thereof (that is, the bulk region of the second metal oxide layer 204b) and is different from the degree of oxygen deficiency of the first metal oxide layer 204a.

By application of the initial break voltage between the first conductive layer 103 and the second conductive layer 106, the local region 105 is formed in the resistive film 204. By the initial break voltage, there can be formed the local region 105 which is in contact with the second conductive layer 106, which penetrates the second metal oxide layer 204b and partially enters the first metal oxide layer 204a, and which is not in contact with the first conductive layer 103.

Next, one evaluation example of the gas sensor cell formed as described above will be described.

Figure 5:
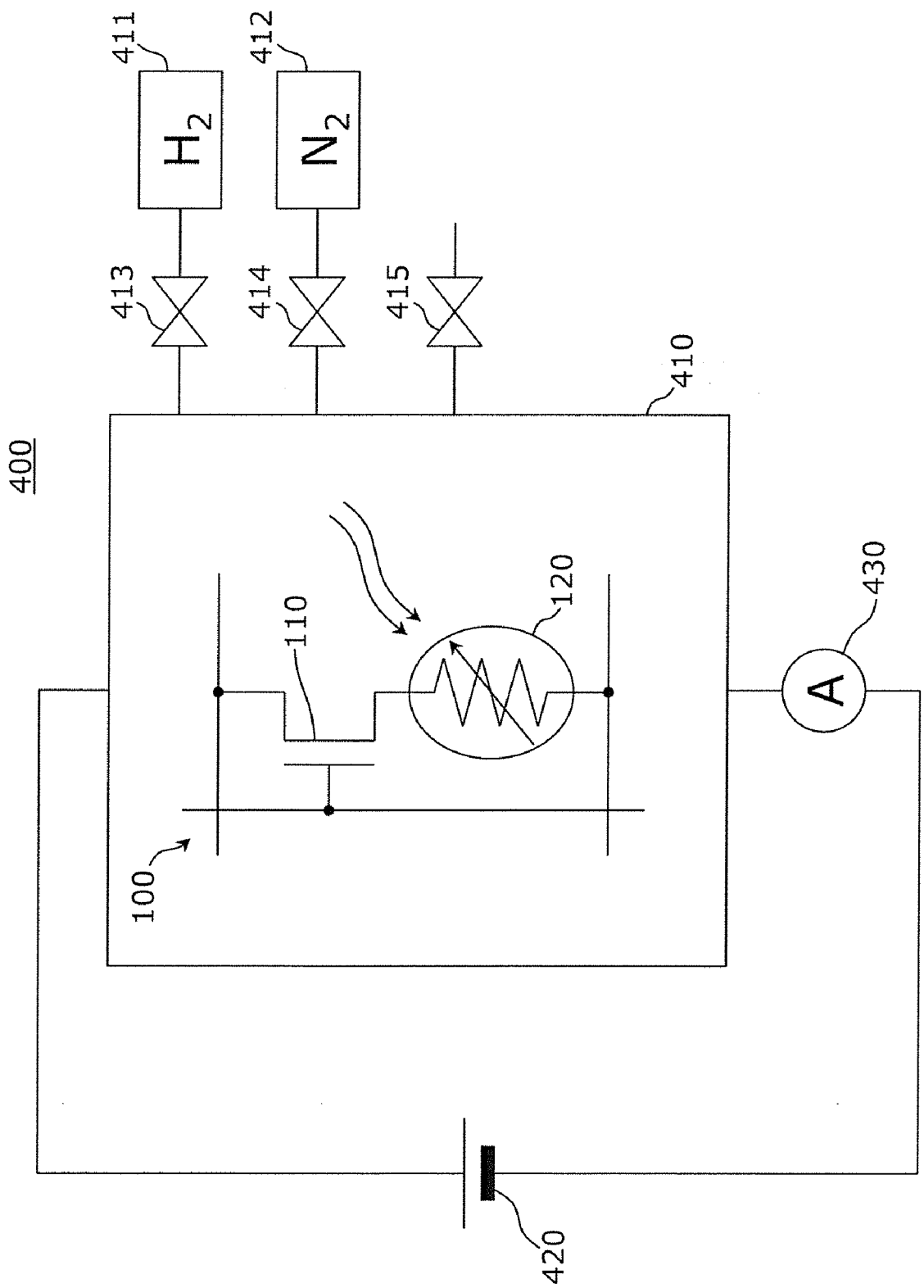
FIG. 5 is a schematic view showing an evaluation system of the gas sensor cell according to the first embodiment.

FIG. 5 is a block diagram showing one example of an evaluation system used for the evaluation of the gas sensor cell. An evaluation system 400 shown in FIG. 5 includes an air-tight container 410 receiving the gas sensor cell 100, a power source 420, and a current meter 430. The air-tight container 410 is connected to a hydrogen cylinder 411 and a nitrogen cylinder 412 through introduction valves 413 and 414, respectively, and is also configured so that a gas in the container 410 is dischargeable through an exhaust valve 415.

Figure 6:
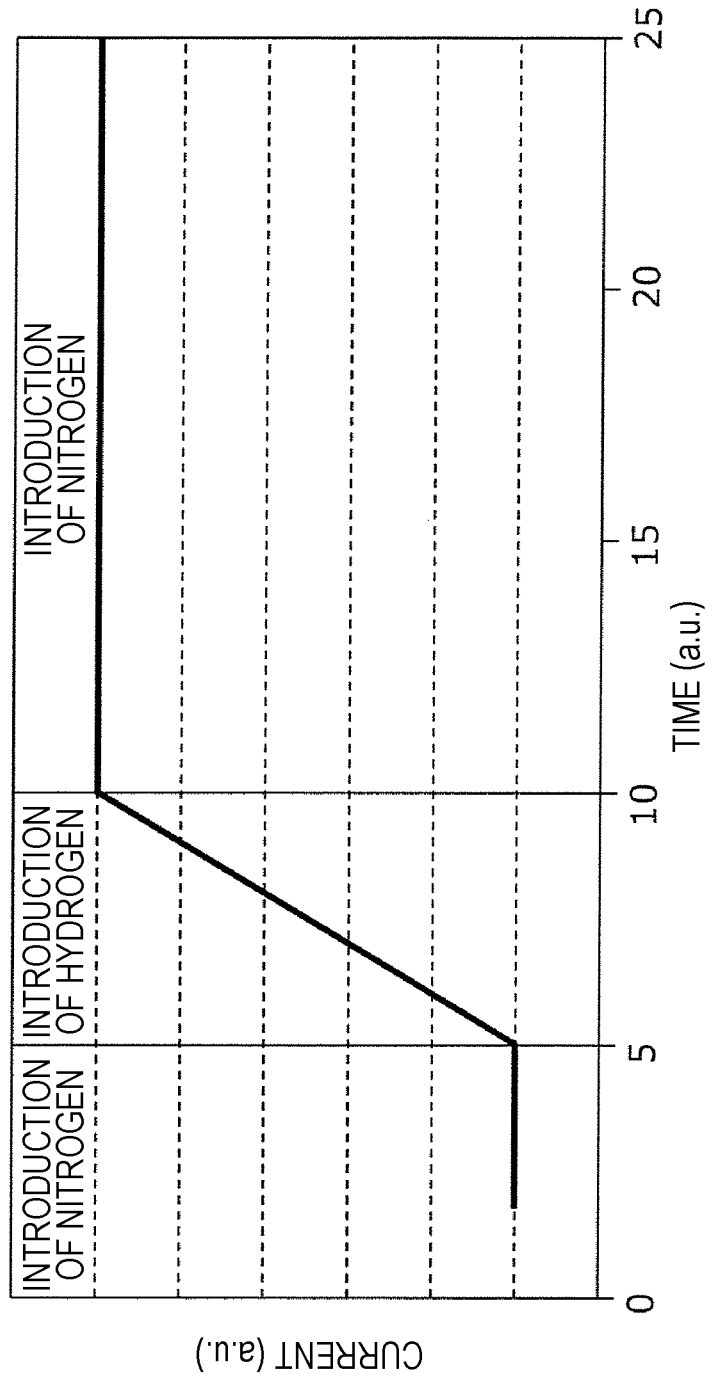
FIG. 6 is a graph showing one example of an evaluation result of the gas sensor cell according to the first embodiment.

FIG. 6 is graph showing one evaluation result of the gas sensor cell 100. The horizontal axis indicates the time (a. u.), and the vertical axis indicates a current (a. u.) flowing between the first conductive layer 103 and the second conductive layer 106. In this experiment, first, a nitrogen gas was charged into the air-tight container 410 in which the gas sensor cell 100 was placed, a hydrogen gas was then charged, and furthermore, a nitrogen gas was again charged.

FIG. 6 shows the result of this evaluation, and along the horizontal axis, three types of periods, that is, the period for nitrogen introduction, the period of hydrogen introduction, and the period of subsequent nitrogen introduction, are shown. It is found that after the introduction gas was switched from a nitrogen gas to a hydrogen gas, the current was started to increase. In addition, even when the introduction gas was again switched from a hydrogen gas to a nitrogen gas, the current was not again decreased.

That is, in the gas sensor cell 100, when the second conductive layer 106 is in contact with a gas (in this case, a hydrogen gas) containing a hydrogen molecule having a hydrogen atom, the resistance between the first conductive layer 103 and the second conductive layer 106 is decreased. In addition, it is understood that after the resistance is decreased as described above, even when the second conductive layer 106 is in contact with a gas (in this case, a nitrogen gas) having no hydrogen atom, the gas sensor cell 100 has a characteristic of retaining this resistance decreased state. In addition, in the gas sensor cell 200, a resistance change characteristic similar to that described above is also observed.

Based on this characteristic, when a hydrogen-containing gas is again monitored using a gas sensor element in which the resistance is decreased in response to a hydrogen-containing gas, in order to more clearly detect the decrease in resistance, the gas sensor element may be set in a high resistive state by applying a setting voltage thereto.

Figure 7:
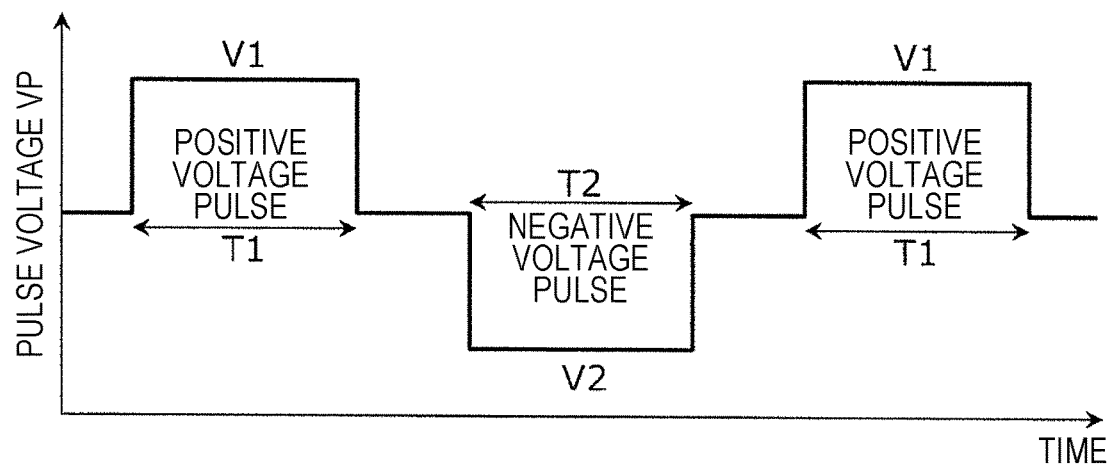
FIG. 7 is a timing chart showing one example of a setting voltage pulse to be applied to the gas sensor cell according to the first embodiment.

FIG. 7 is a timing chart showing a setting voltage pulse to be applied to the gas sensor cell 100. An example in FIG. 7 shows a voltage pulse to be applied to the gas sensor cell 100 in order to set the resistive state of the gas sensor cell 100 in which the second conductive layer 106 is formed of platinum (Pt). The vertical axis indicates a voltage VP of the voltage pulse to be applied between the second wire 132 (bit line) and the first wire 131 (source line) shown in FIG. 2, and the horizontal axis indicates the time. In this case, a polar voltage pulse which applies a higher voltage to the second wire 132 than that to the first wire 131 is a positive voltage pulse, and a polar voltage pulse which applies a lower voltage to the second wire 132 than that to the first wire 131 is a negative voltage pulse.

When the gas sensor element 120 is set in a high resistive (HR) state, as one example, a gate voltage VG of 2.4 V is applied to the third wire 133 (gate electrode), and a voltage pulse having a voltage V1 of +2.5 V and a pulse width T1 of 500 ns is applied to the second wire 132 (bit line). In this case, the ground potential is applied to the first wire 131 (source line). That is, by application of a positive voltage pulse of +2.5 V (high resistive voltage pulse), the gas sensor element 120 is set in a high resistive state.

When the gas sensor element 120 is set in a low resistive (LR) state, as one example, a gate voltage VG of 2.4 V is applied to the third wire 133 (gate electrode), and a voltage pulse having a voltage V2 of +1.5 V and a pulse width T2 of 500 ns is applied to the first wire 131 (source line). In this case, the ground potential is applied to the second wire 132 (bit line). That is, by application of a negative voltage pulse of −1.5 V (low resistive voltage pulse), the gas sensor element 120 is set in a low resistive state.

Figure 8:
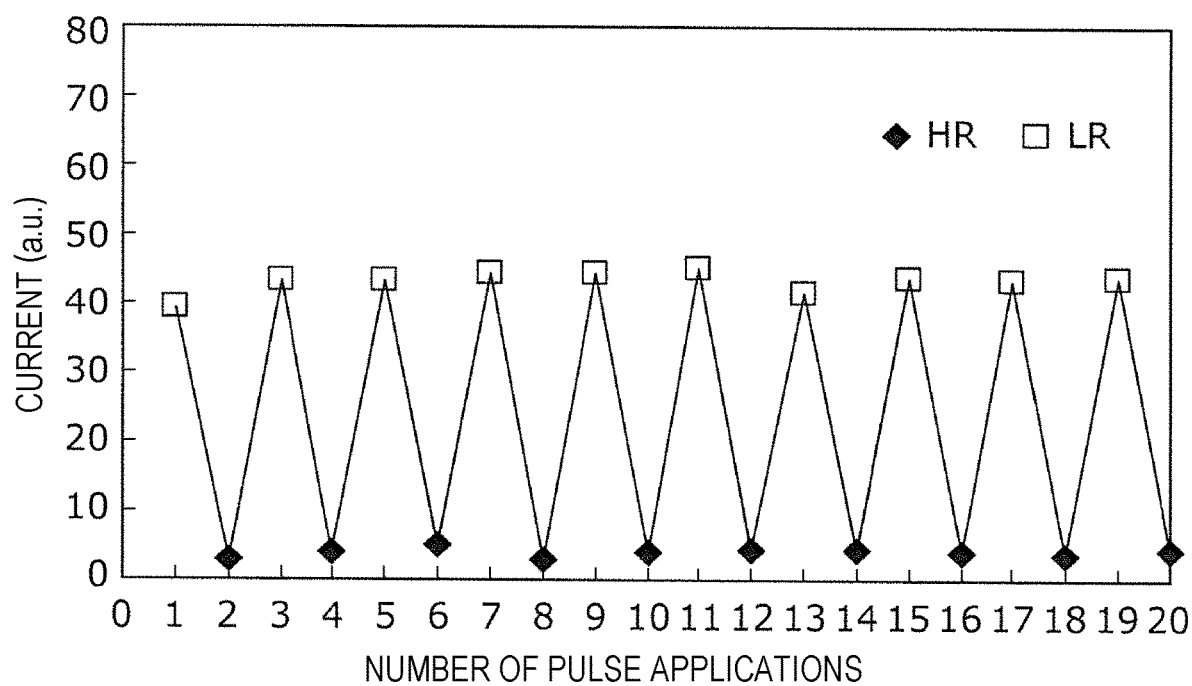
FIG. 8 is a graph showing one example of a resistance change of the gas sensor cell according to the first embodiment by alternate application of a positive and a negative voltage pulse.

FIG. 8 is a graph showing the resistance change by alternate application of a positive and a negative voltage pulse to the gas sensor cell 100. When the application of a setting voltage is stopped at a point at which the gas sensor cell 100 is in a high resistive state, the gas sensor cell 100 is in a standby state suitable for detection of a hydrogen-containing gas in which the decrease in resistance can be more clearly detected. In addition, even after the resistance is decreased by detecting a hydrogen-containing gas, when a voltage pulse similar to that described above is applied, the gas sensor cell 100 can be again set in a high resistive state.

Second Embodiment

In a second embodiment, the structure of an important portion of a gas sensor cell array including gas sensor cells and a control method of the gas sensor cell array will be described.

Figure 9:
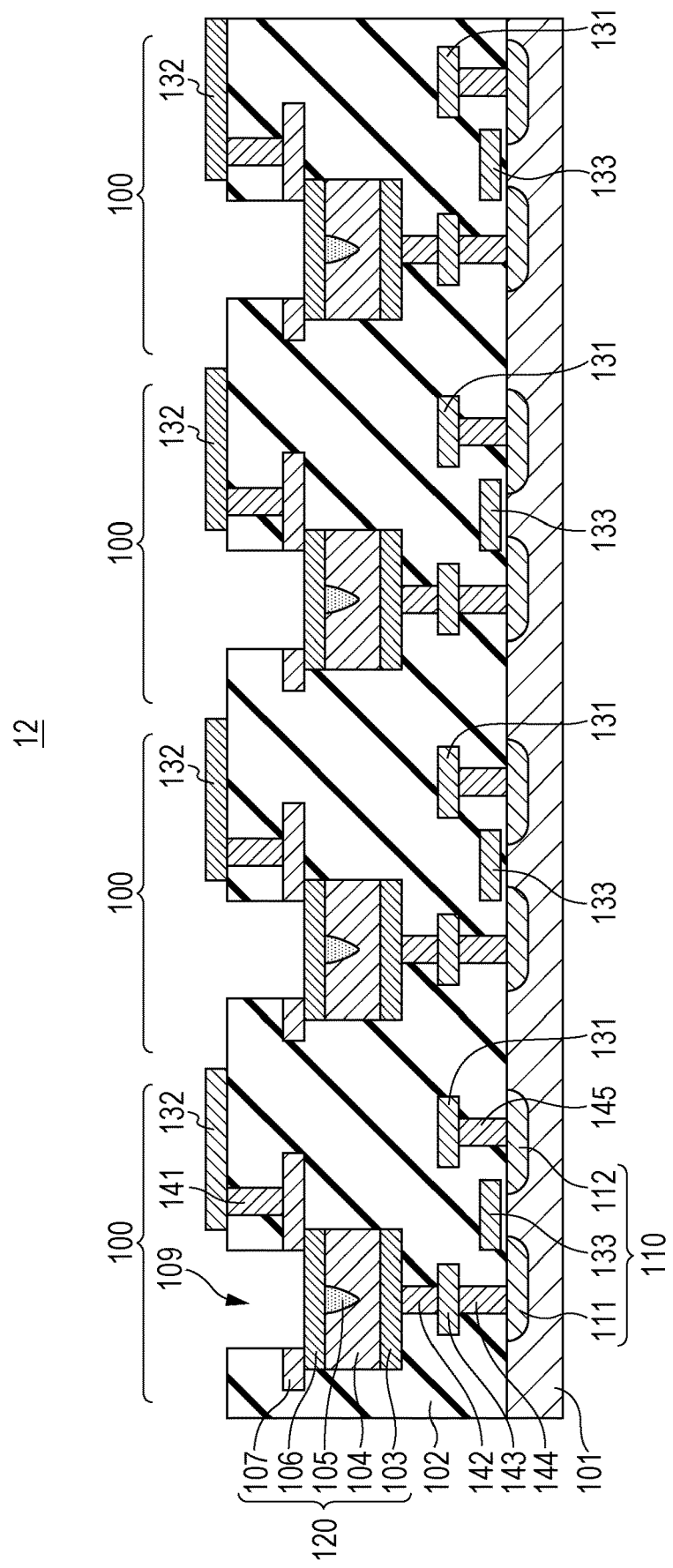
FIG. 9 is a cross-sectional view showing one example of a portion including gas sensor cells of a gas sensor cell array according to a second embodiment.

FIG. 9 is a cross-sectional view showing a portion including gas sensor cells of the gas sensor cell array. FIG. 9 shows one example of a cross-sectional structure of a portion 12 shown in FIG. 1A and the structure in which four gas sensor cells 100 each shown in FIG. 2 are arranged.

Although not shown in the figure, the first wires 131 are connected to each other, and the second wires 132 are connected to each other, so that a source line SL0 and a bit line BL0 are formed, respectively. The third wires 133 are formed to extend in a direction intersecting the plane of this figure, so that word lines WL0, WL1, WL2, and WL3 are formed.

The structure shown in FIG. 9 is formed to extend in a direction parallel to the plane of the figure and a direction intersecting the plane of the figure, so that the gas sensor cell array 10 including many gas sensor cells 100 can be formed.

In addition, in FIG. 9, although the first conductive layer 103, the resistive film 104, and the second conductive layer 106 are provided separately for each gas sensor cell 100, the gas sensor cell 100 is not limited to the example described above. For example, one of the first conductive layer 103 and the second conductive layer 106, and the resistive film 104 each may be formed commonly over the gas sensor cells.

Figure 10:
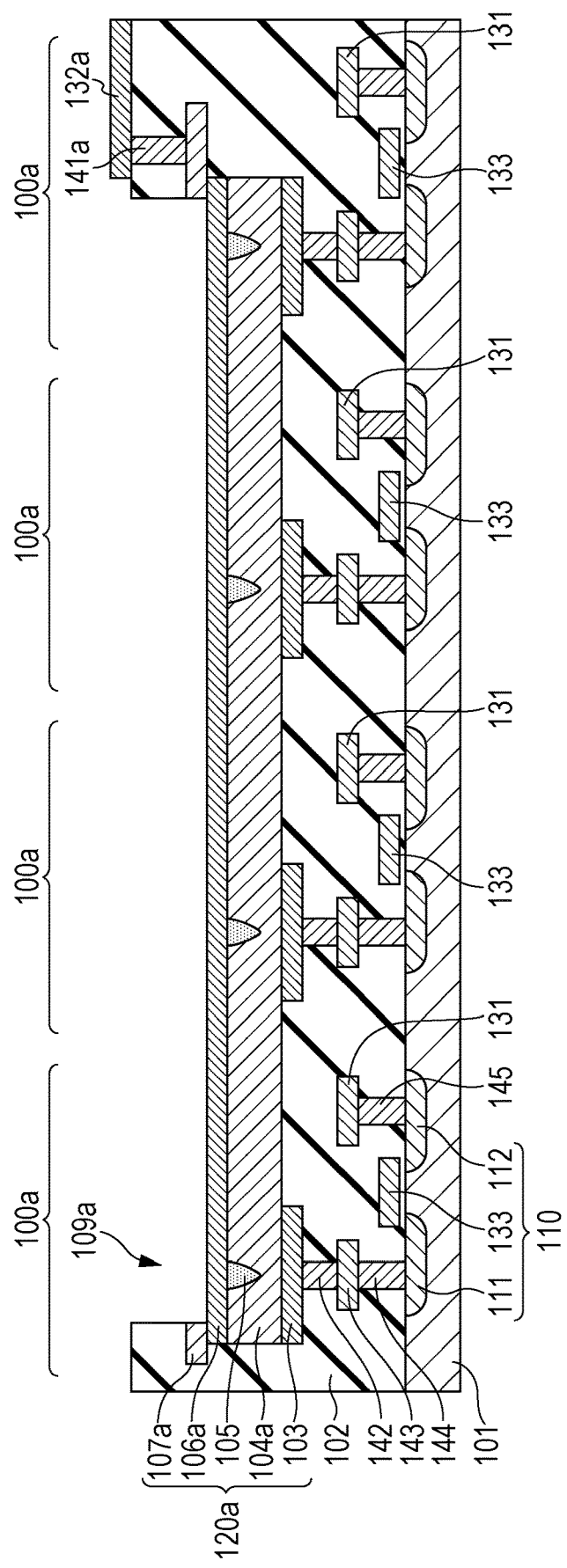
FIG. 10 is a cross-sectional view showing a modified example of the portion including the gas sensor cells of the gas sensor cell array according to the second embodiment.

FIG. 10 is a cross-sectional view showing a portion 12a obtaining by modification of the portion 12 shown in FIG. 9. In the portion 12a shown in FIG. 10, a resistive film 104a, a second conductive layer 106a, and an opening 109a of a gas sensor element 120a are each formed commonly over gas sensor cells 100a. In addition, the arrangement of a third conductive layer 107a, a second wire 132a, and a via 141a is changed.

According to the structure shown in FIG. 10, the initial break voltage is applied between the common second conductive layer 106a and each of the first conductive layers 103, so that the local region 105 may be formed in each gas sensor element 120a.

Figure 11:
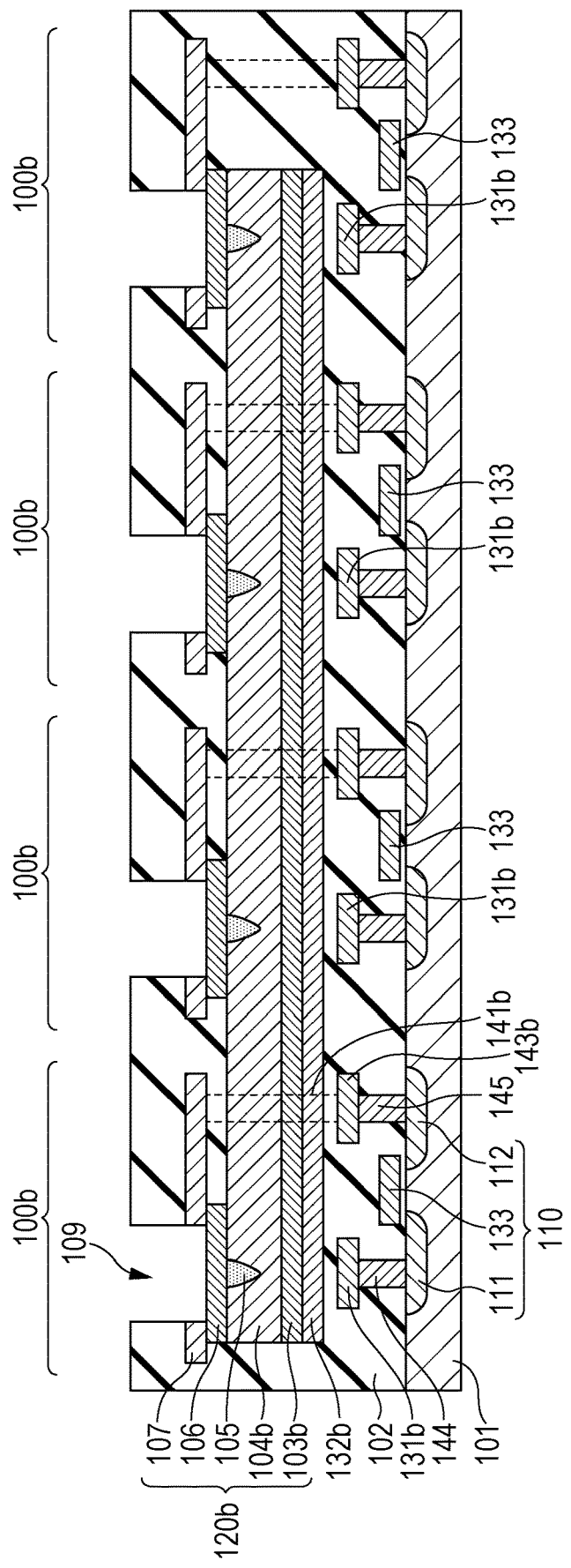
FIG. 11 is a cross-sectional view sowing a modified example of the portion including the gas sensor cells of the gas sensor cell array according to the second embodiment.

FIG. 11 is a cross-sectional view of a portion 13 formed by another modification of the portion 12 shown in FIG. 9. FIG. 11 shows one example of a cross-sectional structure of the portion 13 shown in FIG. 1C. In the portion 13 shown in FIG. 11, a first conductive layer 103b and a resistive film 104b of a gas sensor element 120b are each formed commonly over gas sensor cells 100b. In addition, the arrangement of a first wire 131b, a second wire 132b, vias 141b, and lower wires 143b is changed. The vias 141b are provided outside the figure and each connect the third conductive layer 107 to the lower wire 143b.

According to the structure shown in FIG. 11, the initial break voltage is applied between the common first conductive layer 103b and each of the second conductive layers 106, so that the local region 105 may be formed in each gas sensor element 120b.

By any one of the structures shown in FIGS. 9, 10, and 11, a gas sensor cell array including the gas sensor cells 100, 100a, or 100b can be obtained.

In each of the gas sensor cells 100, 100a, and 100b, the local region 105 is formed right under a portion at which the second conductive layer 106 or 106a is exposed. Hence, the time required for hydrogen of a hydrogen-containing gas to reach the local region can be shortened, and hence, a gas sensor excellent in detection of a hydrogen-containing gas can be obtained.

In addition, among the gas sensor cells, at least one gas sensor cell which is arbitrarily selected is connected by the first wires 131 or 131b, the second wires 132, 132a, or 132b, and the third wires 133 so that the setting operation and the sensing operation of the resistive state can be performed. Hence, according to the gas sensor cell array described above, for example, while the at least one gas sensor cell is sequentially selected under the control of an exterior control circuit, in a selected gas sensor cell, the setting operation and the sensing operation of the resistive state can be performed.

The setting operation and the sensing operation of the resistive state can be performed, for example, as described below.

Figure 12:
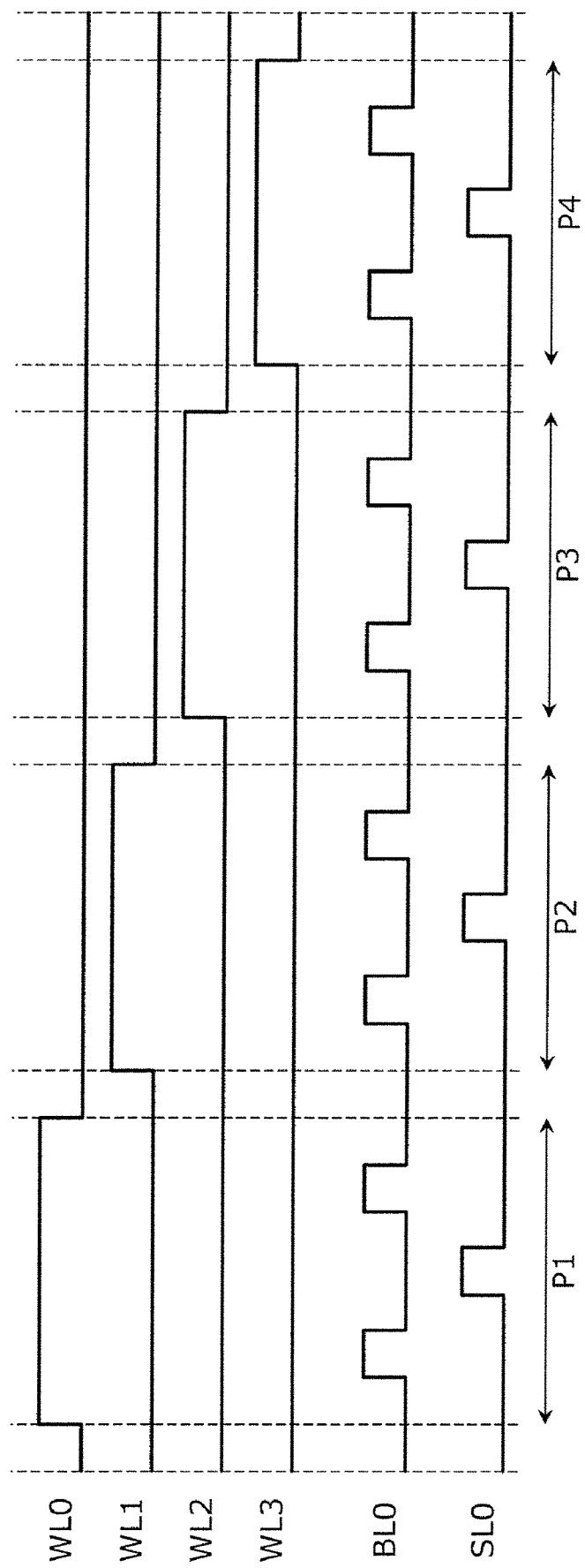
FIG. 12 is a timing chart showing one example of a setting voltage pulse to be applied to the gas sensor cell array according to the second embodiment.

FIG. 12 is a timing chart showing one example of the setting voltage pulse to be applied to the gas sensor cell array. The timing chart shown in FIG. 12 corresponds to the operation of setting the resistive states of the four gas sensor cells 100 included in the portion 12 shown in FIG. 1A.

Hereinafter, for the convenience of description, the gas sensor cells 100 connected to the word lines WL0, WL1, WL2, and WL3 are represented by gas sensor cells SC0, SC1, SC2, and SC3, respectively.

In a period P1, a gate voltage VG of 2.4 V is applied to the word line WL0, and a gate voltage VG of 0 V (ground potential) is applied to the word lines WL1, WL2, and WL3. Accordingly, among the gas sensor cells SC0, SC1, SC2, and SC3, the selection element 110 of the gas sensor cell SC0 is set in a conductive state.

To the gas sensor cell SC0, a positive voltage pulse, a negative voltage pulse, and a positive voltage pulse are sequentially applied through the bit line BL0 and the source line SL0. Accordingly, after being set in a high resistive state and then set in a low resistive state, the gas sensor cell SC0 is set in a high resistive state.

In this case, it has been known that compared to a high resistive state set by application of a single positive voltage pulse, the high resistive state set by application of the three voltage pulses, that is, a positive voltage pulse, a negative voltage pulse, and a positive voltage pulse, is stably maintained for a long period of time. Hence, by application of the above three voltage pulses, the gas sensor cell SC0 can be stably maintained for a long period of time in a standby state suitable for detection of a hydrogen-containing gas. In addition, as for this application of three voltage pulses, that is, a positive voltage pulse, a negative voltage pulse, and a positive voltage pulse, after the three voltage pulses are repeatedly applied in this order at least two times, a positive voltage pulse may be finally applied.

In the following periods P2, P3, and P4, the setting operation similar to that described above is performed on each of the gas sensor cells SC1, SC2, and SC3.

The setting operation as described above is one example of a method for controlling a gas sensor in which after a predetermined number of gas sensor cells (in the above case, the number is one) are sequentially selected from a plurality of gas sensor cells, the setting operation of the resistive state is performed on each of the selected gas sensor cells.

Figure 13:
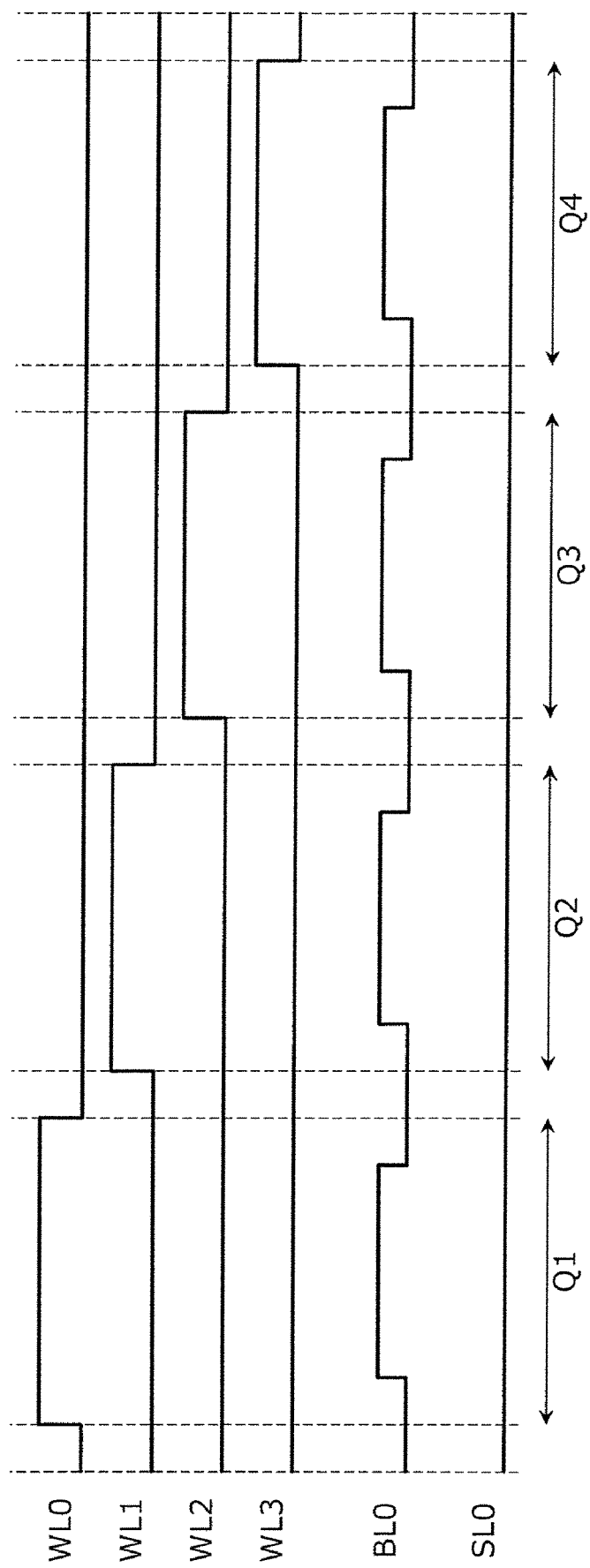
FIG. 13 is a timing chart showing one example of a sensing voltage pulse to be applied to the gas sensor cell array according to the second embodiment.

FIG. 13 is a timing chart showing one example of the sensing voltage pulse to be applied to the gas sensor cell array. The timing chart shown in FIG. 13 corresponds to the operation of sensing the resistive states of the four gas sensor cells 100 included in the portion 12 shown in FIG. 1A.

In a period Q1, a gate voltage VG of 2.4 V is applied to the word line WL0, and a gate voltage VG of 0 V (ground potential) is applied to the word lines WL1, WL2, and WL3. Accordingly, among the gas sensor cells SC0, SC1, SC2, and SC3, the selection element 110 of the gas sensor cell SC0 is set in a conductive state.

A positive voltage pulse is applied to the gas sensor cell SC0 through the bit line BL0 and the source line SL0, and a current flowing between the bit line BL0 and the source line SL0 is measured. The amplitude of a positive voltage pulse used for the sensing operation is smaller than that of a positive voltage pulse used for the setting operation. As one example, the voltage of the positive voltage pulse for the sensing operation is +0.6 V, and the pulse width may be 500 ns.

In the following periods Q2, Q3, and Q4, the sensing operation similar to that described above is performed on each of the gas sensor cells SC1, SC2, and SC3.

The sensing operation as described above is one example of a method for controlling a gas sensor in which after a predetermined number of gas sensor cells (in the above case, the number is one) are sequentially selected from a plurality of gas sensor cells, the sensing operation of the resistive state is performed on each of the selected gas sensor cells.

When the gas sensor cell array is controlled in accordance with the above setting operation and sensing operation, without instantaneously consuming a large operation electrical power, the setting operation and the sensing operation of the resistive state can be performed on all the gas sensor cells. As a result, a gas sensor cell capable of simultaneously achieving a low power consumption and a high sensitivity can be obtained.

Third Embodiment

Figure 14:
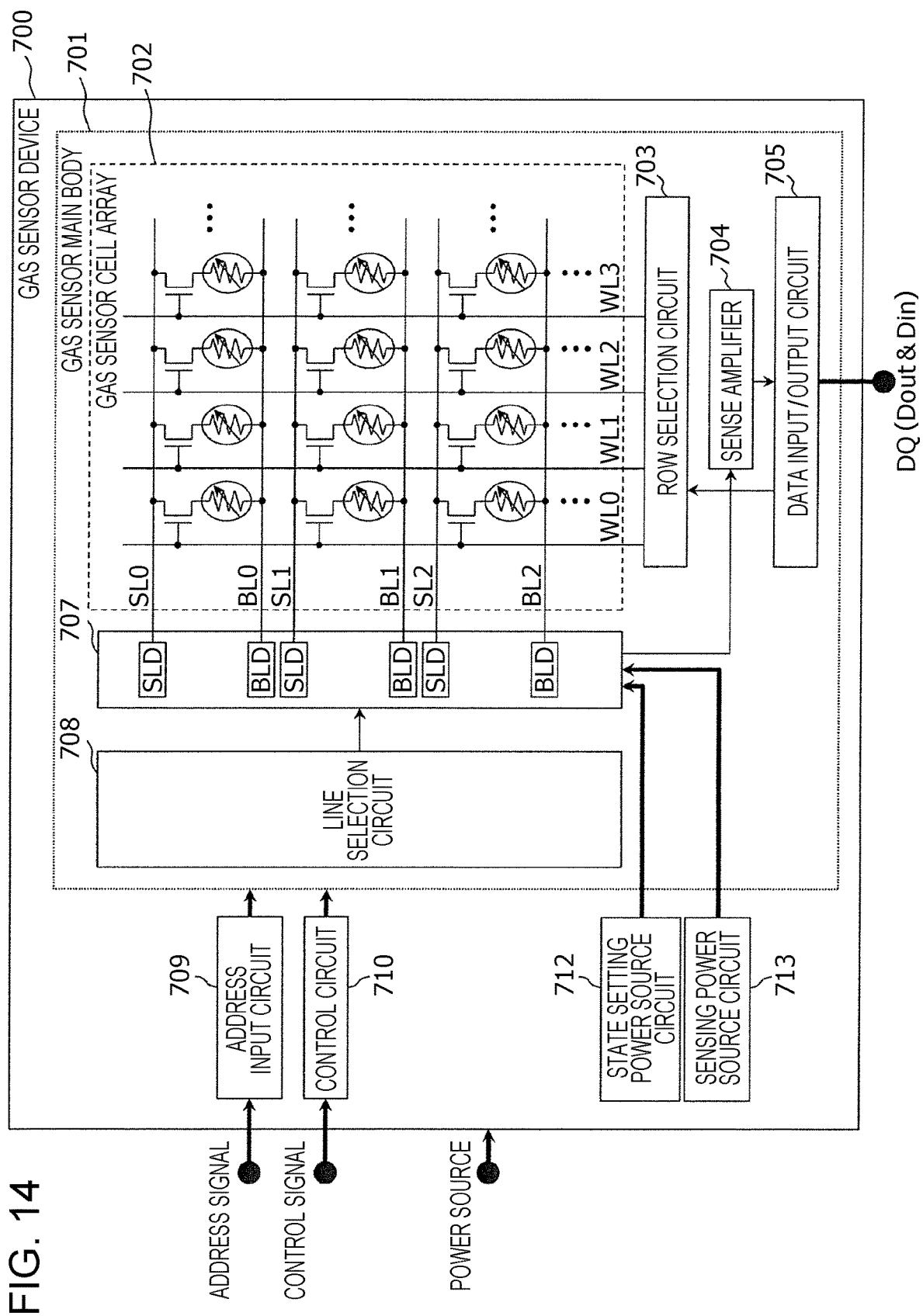
FIG. 14 is a block diagram showing a functional structural example of a gas sensor device according to a third embodiment.

FIG. 14 is a block diagram showing one example of a functional structure of a gas sensor device according to a third embodiment.

As shown in FIG. 14, a gas sensor device 700 includes a gas sensor main body 701 on a semiconductor substrate. The gas sensor main body 701 includes a gas sensor cell array 702, a line selection circuit 708, a line driver 707 including bit line drivers BLD and source line drivers SLD, a row selection circuit 703, a sense amplifier 704, and a data input/output circuit 705. The sense amplifier 704 detects a current flowing through a selected bit line and represents a high resistive state by data "0" and a low resistive state which is caused by voltage application or hydrogen detection by data "1". The data input/output circuit 705 performs an input/output treatment of an input/output data through a terminal DQ. As the gas sensor cell array 702, for example, the gas sensor cell array 10 or 20 described in the first and the second embodiments is used.

Furthermore, the gas sensor device 700 also includes an address input circuit 709 receiving an address signal input from the outside, a control circuit 710 controlling the operation of the gas sensor main body 701 in accordance with a control signal input from the outside, a state setting power source circuit 712, and a sensing power source circuit 713.

The control circuit 710 instructs, in the setting operation, the application of a setting voltage in accordance with an input data Din input in the data input/output circuit 705. In addition, the control circuit 710 outputs, in the sensing operation, a reading signal which instructs the sensing operation to the sense amplifier 704.

The line selection circuit 708 receives a line address signal output from the address input circuit 709 and applies a predetermined voltage in accordance with this line address signal to a selected bit line/a source line by a bit line driver circuit BLD and a source line driver circuit SLD of the line driver 707 corresponding to one of a plurality of bit line/source line pairs of BL0, BL1, and BL2 and SL0, SL1, and SL2.

The row selection circuit 703 receives a row address signal output from the address input circuit 709 and applies a predetermined voltage in accordance with this row address signal to a word line selected from a plurality of word lines WL0, WL1, WL2, WL3 - - - .

According to the gas sensor device 700 formed as described above, under the control of the control circuit 710, the setting operation and the sensing operation of the resistive state are performed on at least one gas sensor cell to be sequentially selected.

In this case, the line selection circuit 708 and the row selection circuit 703 form a selection circuit selecting at least one gas sensor cell 100 from the gas sensor cell array 702.

In addition, the sense amplifier 704 forms a measurement circuit measuring a current flowing in the gas sensor cell 100 upon application of a sensing voltage to the gas sensor cell 100 in which the selection element 110 is in a conductive state.

In addition, the state setting power source circuit 712 forms a restoration circuit applying a setting voltage to the gas sensor cell 100 in order to increase the resistance of the gas sensor element 120, the resistance of which is decreased in response to a gas containing a gas molecule having a hydrogen atom.

The gas sensor device 700 may be formed, for example, as a semiconductor integrated circuit (IC) chip or may be formed as an IC card using a flexible substrate formed from a resin material.

Figure 15:
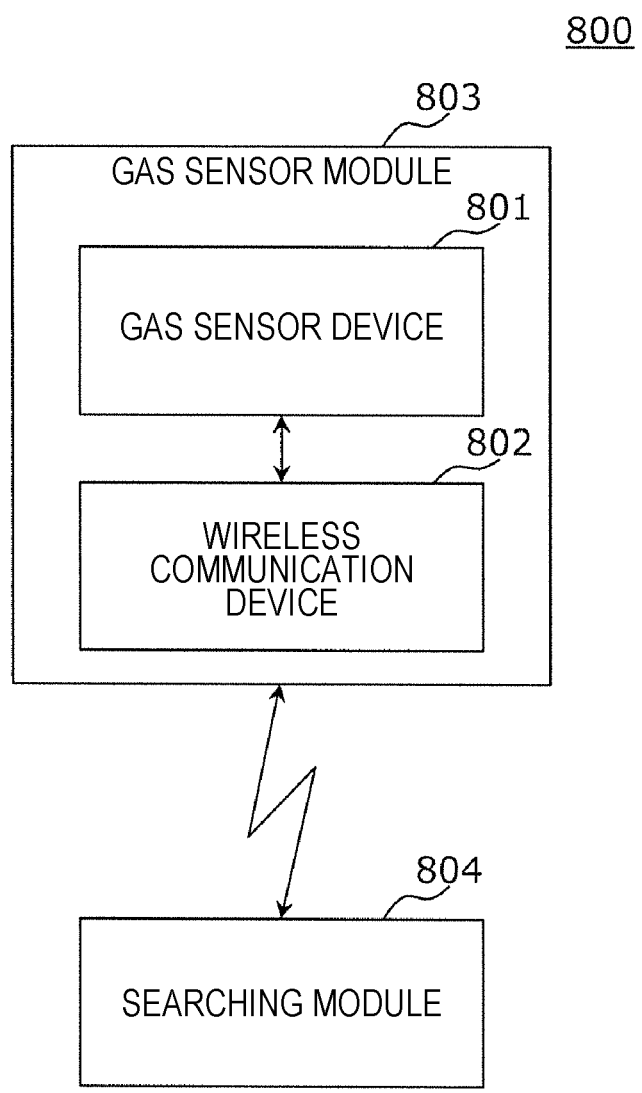
FIG. 15 is a functional block diagram showing a structural example of a gas sensing system according to the third embodiment.

FIG. 15 is a block diagram showing a gas sensing system according to the third embodiment.

As shown in FIG. 15, a gas sensing system 800 includes on a substrate, a gas sensor module 803 formed of a gas sensor device 801 and a wireless communication device 802. As the gas sensor device 801, for example, the gas sensor device 700 described above is used.

The wireless communication device 802 may be selected from communication units, such as an infrared communication unit, a Bluetooth (registered trade name) communication unit, a radio frequency (RF) communication unit, and a wireless/fidelity (WiFi) communication unit.

The gas sensor device 801 and the wireless communication device 802 are electrically connected to each other, and the gas sensor device 801 obtains all the address signal, the control signal, and the power source shown in FIG. 14 from the wireless communication device 802.

The gas sensor module 803 is operated after obtaining the address signal, the control signal, and the power source from an exterior searching module 804 by the wireless communication device 802 and uploads the information whether a hydrogen-containing gas is detected or not in the gas sensor device 801 to the searching module 804.

As described above, according to the gas sensing system 800, since the power source is formed in a contactless manner, the device itself does not function as an ignition point, and hence a complicated explosion protection treatment is not required. As a result, a gas sensing system formed from simple devices can be obtained.

Figure 16:
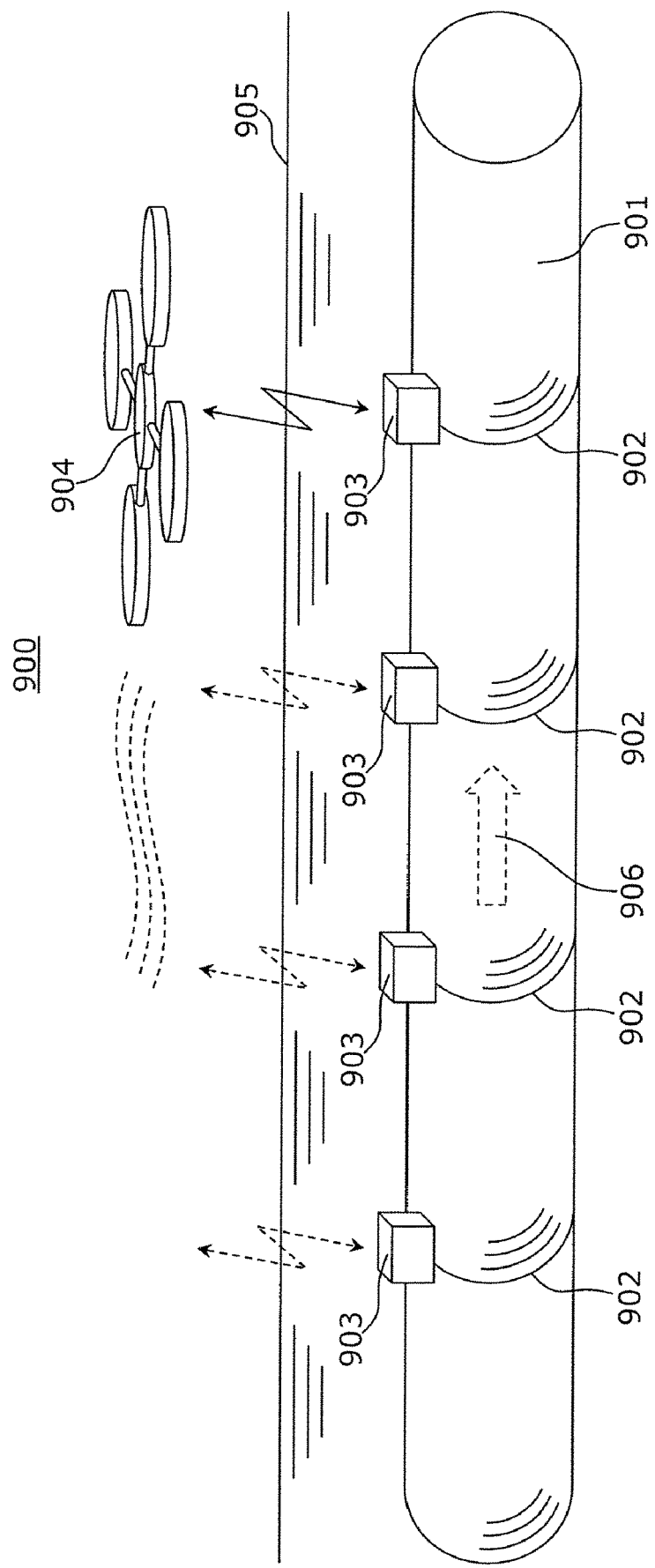
FIG. 16 is a schematic view showing an application example of the gas sensing system according to the third embodiment.

FIG. 16 is a schematic view showing a gas-leakage monitoring system of a gas pipe line using the gas sensing system 800 shown in FIG. 15.

As shown in FIG. 16, the gas-leakage monitoring system 900 of a gas pipe line includes a searching module 904 and gas sensor modules 903 which are buried in a ground 905 and are disposed at respective ferrules 902 (at four places in the example shown in FIG. 9) of a gas pipe 901 transporting a gas 906. For the gas sensor module 903 and the searching module 904, for example, the gas sensor module 803 and the searching module 804 of the gas sensing system 800 described above may be used. In addition, the gas sensor module 903 may be disposed in contact with the gas pipe 901 or may be disposed apart from the gas pipe 901. Furthermore, the gas sensor module 903 may be disposed at a position other than that of the ferrule 902 and, for example, may be disposed at a place in the vicinity of the ferrule 902.

The searching module 904 sequentially communicates with the gas sensor modules 903 by scanning along a gas pipe line while being carried by a gas-leakage monitoring operator or being carried by a drone. As a result, the gas leakage can be detected, and a gas-leakage place can be identified.

In addition, the gas sensing system 800 may be applied not only to the gas-leakage monitoring system 900 of a gas pipe line but also to a gas-leakage monitoring system detecting leakage of a hydrogen-containing gas, for example, in a fuel-cell vehicle, a hydrogen station, a hydrogen plant, or the like.

Supplement

The gas sensor device 700 shown in FIG. 14 is one example of the "gas sensor device" according to the present disclosure. In FIG. 14, the line selection circuit 708 and/or the row selection circuit 703 is one example of the "selection circuit" of the present disclosure. The state setting power source circuit 712 and/or the sensing power source circuit 713 is one example of the "power source circuit" of the present disclosure. The sense amplifier 704 is one example of the "measurement circuit" of the present disclosure. However, in the gas sensor device according to the present disclosure, the selection circuit, the power source circuit, and the measurement circuit are each an arbitrary constituent element. As long as including gas sensor elements and switches, the gas sensor device according to the present disclosure may sufficiently work and may be formed only from the gas sensor cell array 10, 20, 30, or 702. In addition, in the various embodiments described above, the selection element 110 is one example of the "switch" according to the present disclosure. The switch is, for example, a transistor.

In the gas sensor cell array 10 shown in FIG. 1A, the gas sensor cells 100 are connected in parallel. In the gas sensor cell 100, one gas sensor element 120 and one selection element 110 are connected in series.

As shown in FIG. 2, the gas sensor element 120 includes the first conductive layer 103, the resistive film 104 disposed on the first conductive layer 103, and the second conductive layer 106 disposed on the resistive film 104. The resistive film 104 is one example of the "metal oxide layer" according to the present disclosure. The resistive film 104 includes the local region 105 and the bulk region surrounding the local region 105. In this case, the "surrounding the local region 105" is not limited to the case in which all the outer peripheral surface of the local region 105 is surrounded. In FIG. 2, the bulk region is a region of the metal oxide layer 104 other than the local region 105. The degree of oxygen deficiency of the local region 105 is high as compared to that of the bulk region. In FIG. 2, the local region 105 is in contact with the second conductive layer 106 and is not in contact with the first conductive layer 103.

In FIG. 2, the insulation layer 102 has the opening 109. In the opening 109, the second conductive layer 106 is partially exposed from the insulation layer 102. The exposed portion of the second conductive layer 106 can be in contact with a gas.

When a gas having a hydrogen atom is brought into contact with the second conductive layer 106, the resistance of the local region 105 is decreased, the resistance of the resistive film 104 is decreased, and the resistance of the gas sensor element 120 is decreased.

In the gas sensor element according to the present disclosure, the third conductive layer 107 as shown in FIG. 2 is an arbitrary constituent element.

As shown in FIG. 9, the selection elements 110 are disposed on the common substrate 101. The gas sensor elements 120 are disposed above the respective selection elements 110.

In the example shown in FIG. 14, when the line selection circuit 703 and the row selection circuit 708 put at least one of the selection elements 110 in an ON state, at least one of the gas sensor cells 100 is selected. For example, the line selection circuit 703 and the row selection circuit 708 may simultaneously select at least two gas sensor cells 100. The line selection circuit 703 and the row selection circuit 708 may sequentially change a gas sensor cell 100 to be selected and for example, may sequentially select all the gas sensor cells 100. To the gas sensor cell 100 thus selected, the sensing voltage and/or the setting voltage is applied. In addition, the "sensing voltage" described in the above embodiment is one example of the "sense voltage" according to the present disclosure. The "setting voltage" described in the above embodiment is one example of the "predetermined voltage" according to the present disclosure. In addition, the "power source circuit" according to the present disclosure may be, for example, a power source itself or may be a conversion circuit converting the voltage of an exterior power source to a desired voltage.

In the above embodiment, the example in which the gas sensor device 801 included in the gas sensor module 803 is the gas sensor device 700 shown in FIG. 14 has been described. However, the structure of the gas sensor device 801 is not limited thereto. The gas sensor device 801 may be, for example, a single gas sensor element 120 and may also be another gas sensor. In other words, the gas sensing system 800 described above is not limited to a gas sensor having a specific structure and may be appropriately modified. As is the case described above, the gas-leakage monitoring system 900 of a gas pipe line described above is not limited to a gas sensor having a specific structure and may be appropriately modified.

Other Modified Examples

Although the gas sensors, the gas sensing systems, and the methods for controlling a gas sensor according to various aspects of the present disclosure have been described with reference to the embodiments, the present disclosure is not limited to those embodiments. Any modifications of the embodiments performed by a person skilled in the art and any combinations among the constituent elements of the embodiments may be carried out without departing from the scope of the present disclosure and are understood to be included in the present disclosure.

Overview of Embodiments

A gas sensor according to one aspect comprises gas sensor cells disposed on a single substrate; in each of the gas sensor cells, a selection element in which a conductive state and a non-conductive state can be switched therebetween is connected in series to a gas sensor element having a resistance which is decreased in response to a gas containing a gas molecule having a hydrogen atom; and the gas sensor cells are electrically connected to each other.

By the structure as described above, a gas sensor suitable to simultaneously achieve a low power consumption and a high sensitivity can be obtained in which at least one of the gas sensor cells can be sequentially selected and then operated. In the above operation, the sensing operation of the resistive state of the gas sensor cell may be included, and the setting operation of the resistive state of the gas sensor cell may also be included.

In addition, the gas sensor described above may further comprise a selection circuit which puts the selection element of at least one gas sensor cell selected from the gas sensor cells in a conductive state.

By the structure as described above, under the control of the selection circuit, when the selection element of the at least one gas sensor cell selected from the gas sensor cells is put in a conductive state, the at least one gas sensor cell can be operated.

In addition, in each of the gas sensor cells described above, the gas sensor element includes a first conductive layer and a second conductive layer, the respective principal surfaces of which face each other; a metal oxide layer disposed in contact with the principal surface of the first conductive layer and in contact with the principal surface of the second conductive layer; a local region disposed in the metal oxide layer so as to be in contact with the second conductive layer and having a high degree of oxygen deficiency as compared to that of the metal oxide layer; and an insulation layer covering the first conductive layer, the second conductive layer, and the metal oxide layer. At least a portion of the other surface of the second conductive layer facing the principal surface thereof is exposed without being covered with the insulation layer, and when the second conductive layer is in contact with a gas containing a gas molecule having a hydrogen atom, the resistance between the first conductive layer and the second conductive layer may be decreased.

By the structure as described above, a current flowing between the first conductive layer and the second conductive layer is concentrated to the local region having a high degree of oxygen deficiency. As a result, by a small current, the temperature of the local region can be increased.

Since the local region is heated by a current flowing between the first conductive layer and the second conductive layer, a hydrogen atom is dissociated from the gas molecule at a portion at which the second conductive layer and the local region are in contact with each other, and the hydrogen atom thus dissociated is bonded to an oxygen atom in the local region of the metal oxide layer, so that the resistance between the first conductive layer and the second conductive layer is decreased.

In more particular, when the temperature of the local region is increased, the temperature of the surface of the second conductive layer is also increased. In accordance with the increase in temperature, the efficiency of dissociation of a hydrogen atom from a hydrogen molecule at the second conductive layer is increased by the catalyst function thereof. That is, the gas sensitivity of the gas sensor element is activated.

When a hydrogen molecule is brought into contact with the second conductive layer, a hydrogen atom is dissociated from the hydrogen molecule and then reaches the local region by diffusion through the second conductive layer. In addition, since the hydrogen atom is bonded to oxygen of a metal oxide present in the local region to form water ($H_2O$), the degree of oxygen deficiency of the local region is further increased. Hence, a current is likely to flow in the local region, and the resistance between the first conductive layer and the second conductive layer is decreased.

Accordingly, by the use of the gas sensitivity activated by the self-heating in the local region formed inside the metal oxide layer, a hydrogen-containing gas can be detected without performing heating by a heater, and a gas sensor excellent in electrical power saving can be obtained.

In addition, in each of the gas sensor cells, the metal oxide layer is formed by laminating a first metal oxide layer formed of a first metal oxide and a second metal oxide layer formed of a second metal oxide having a low degree of oxygen deficiency as compared to that of the first metal oxide; the first metal oxide layer is in contact with the first conductive layer, and the second metal oxide layer is in contact with the second conductive layer; and the local region penetrates at least the second metal oxide layer so as to be in contact with the second conductive layer and has a high degree of oxygen deficiency as compared to that of the second metal oxide layer.

By the structure as described above, when a laminate structure excellent in resistance change characteristic is used for the metal oxide layer, a gas sensor excellent in detection of a hydrogen-containing gas can be obtained.

In addition, in each of the gas sensor cells, the local region may be present right under a portion at which the second conductive layer is exposed.

By the structure as described above, since the time required for hydrogen of a hydrogen-containing gas to reach the local region can be shortened, a gas sensor excellent in detection of a hydrogen-containing gas can be obtained.

In addition, in each of the gas sensor cells, the second conductive layer may be formed of a material having a catalyst function to dissociate the hydrogen atom from the gas molecule.

By the structure as described above, at the portion at which the second conductive layer and the local region are in contact with each other, a hydrogen atom is dissociated from the hydrogen molecule, and the hydrogen atom thus dissociated is bonded to an oxygen atom in the local region of the metal oxide layer, so that the resistance between the first conductive layer and the second conductive layer is decreased.

In addition, in each of the gas sensor cells, the second conductive layer may be formed of platinum, palladium, iridium, or an alloy containing at least one of platinum, palladium, or iridium.

By the structure as described above, the second conductive layer is able to dissociate a hydrogen atom from the hydrogen molecule by the catalyst function of platinum, palladium, or iridium.

In addition, in each of the gas sensor cells, in accordance with a voltage to be applied between the first conductive layer and the second conductive layer, the metal oxide layer may be reversibly changed between a high resistive state and a low resistive state having a lower resistance than that of the high resistive state.

By the structure as described above, the resistive state of the metal oxide layer can be changed besides the change caused by a hydrogen-containing gas. For example, after the second conductive layer is set in a high resistive state, a gas to be inspected may be brought into contact with the metal oxide layer, and as a result, since the decrease in resistance can be clearly detected, a detection performance of a hydrogen-containing gas is improved.

In addition, when the sensing voltage is applied to a gas sensor cell in which the selection element is in a conductive state, the gas sensor may further include a measurement circuit measuring a current flowing in the gas sensor cell.

By the structure as described above, when the current measured by the measurement circuit is increased, the hydrogen-containing gas can be detected.

In addition, in order to increase the resistance of a gas sensor element, the resistance of which is decreased in response to a gas containing a gas molecule having a hydrogen atom, the gas sensor may further include a restoration circuit applying the setting voltage to the gas sensor cell.

By the structure as described above, after the resistive state of the metal oxide layer is set in a high resistive state, a gas to be inspected can be brought into contact with the second conductive layer. As a result, the decrease in resistance can be clearly detected, and hence a detection performance of a hydrogen-containing gas is improved.

In addition, the restoration circuit may apply to the gas sensor cell as the setting voltage, a first voltage pulse setting the gas sensor element in a high resistive state, a second voltage pulse setting the gas sensor element in a low resistive state, and a third voltage pulse again setting the gas sensor element in a high resistive state in this order.

It has been known that by the setting voltage as described above, the high resistive state set by the application of the above three voltage pulses is stably maintained for a long period of time as compared to a high resistive state set by a single voltage pulse. Hence, the gas sensor element can be stably maintained for a long period of time in a standby state suitable for detection of a hydrogen-containing gas.

In addition, in each of the gas sensor cells, the selection element may be formed of an N-type metal oxide semiconductor (NMOS) transistor.

By the structure as described above, since the selection element is formed of an NMOS transistor having a simple structure and excellent electrical characteristics, a gas sensor suitable to simultaneously achieve a low power consumption and a high sensitivity can be obtained.

In addition, the gas sensor may further include first wires, second wires, and third wires. In each of the gas sensor cells, a first terminal of the selection element may be connected to one of the first wires, a second terminal of the selection element may be connected to a first terminal of the gas sensor element, a second terminal of the gas sensor element may be connected to one of the second wires, and a control terminal of the selection element may be connected to one of the third wires.

In this case, the first wires and the second wires may extend in a first direction, and the third wires may extend in a second direction intersecting the first direction. Alternatively, the first wires and the third wires may extend in a first direction, and the second wires may extend in a second direction intersecting the first direction.

By the structure as described above, since a predetermined electrical signal is supplied through the first wires, the second wires, and the third wires, at least one gas sensor cell can be operated after being selected from the gas sensor cells.

In addition, in the gas sensor, the setting operation of the resistive state of the gas sensor cell or the gas sensing operation may be performed in each of a predetermined number of gas sensor cells sequentially selected from the gas sensor cells.

By the structure as described above, in all the gas sensor cells, without instantaneously consuming a large operation electrical power, the setting operation of the resistive state of the gas sensor cell or the gas sensing operation can be performed. As a result, a gas sensor suitable to simultaneously achieve a low power consumption and a high sensitivity can be obtained.

A gas sensor module according to one aspect comprises the gas sensor described above and a wireless communication device capable of performing wireless communication with an exterior device, and since the wireless communication device is operated by a control signal from an exterior searching module, the gas sensor communicates with the searching module.

By the structure as described above, in the gas sensor module, the advantages of the gas sensor simultaneously achieving a low power consumption and a high sensitivity can be obtained. The operation electrical power of the gas sensor may be wirelessly transmitted from the searching module, and in this case, since the power source is formed in a contactless manner, the gas sensor module itself does not function as an ignition point; hence, a complicated explosion protection treatment is not required. As a result, a gas sensor module which can be easily installed is obtained.

A control method according to one aspect is a method for controlling a gas sensor. The gas sensor comprises gas sensor cells disposed on a single substrate; in each of the gas sensor cells, a selection element in which a conductive state and a non-conductive state can be switched therebetween is connected in series to a gas sensor element having a resistance which is decreased in response to a gas containing a gas molecule having a hydrogen atom; and the gas sensor cells are electrically connected to each other. In the control method described above, a predetermined number of gas sensor cells are sequentially selected from the gas sensor cells, and the setting operation of the resistive state of the gas sensor cell or the gas sensing operation is performed on each of the gas sensor cells thus selected.

By the method as described above, since the setting operation of the resistive state of the gas sensor cell or the gas sensing operation can be performed in all the gas sensor cells without instantaneously consuming a large operation electrical power, in the gas sensor, a low power consumption and a high sensitivity can be simultaneously achieved.

The gas sensor according to the present disclosure may be applied, besides to a gas pipe line, to a fuel-cell vehicle, a hydrogen station, a hydrogen plant, and the like.

What is claimed is:

1. A gas sensor device comprising:
   gas sensors; and
   switches connected to the respective gas sensors in series,
   wherein the gas sensors each include:
      a first conductive layer;
      a second conductive layer;
      a metal oxide layer disposed between the first conductive layer and the second conductive layer, the metal oxide layer including a bulk region and a local region surrounded by the bulk region, a degree of oxygen deficiency of the local region being higher than that of the bulk region; and
      an insulation layer covering the first conductive layer, the second conductive layer, and the metal oxide layer the insulation layer having an opening from which a portion of the second conductive layer is exposed, and
   wherein resistances of the gas sensors are each decreased when a gas containing a hydrogen atom comes into contact with the second conductive layer,
   the switches are transistors,
   the transistors are disposed on a common substrate, and
   the gas sensors are disposed on the respective transistors.

2. The gas sensor device according to claim 1, further comprising:
   selection circuitry that selects at least one gas sensor from the gas sensors by turning on at least one of the switches.

3. The gas sensor device according to claim 2, further comprising:
   power source circuitry that applies a sense voltage to the selected at least one gas sensor.

4. The gas sensor device according to claim 3, further comprising:
   measurement circuitry that measures a current flowing through the selected at least one gas sensor when the sense voltage is applied to the selected at least one sensor.

5. The gas sensor device according to claim 4,
   wherein the power circuitry further applies a predetermined voltage to the selected at least one gas sensor to increase resistance of the selected at least one gas sensor, before the measurement circuitry measures the current.

6. The gas sensor device according to claim 5,
   wherein the predetermined voltage includes a first voltage pulse having a first polarity, a second voltage pulse having a second polarity opposite to the first polarity, and a third voltage pulse having the first polarity in this order.

7. The gas sensor device according to claim 2,
   wherein the selected at least one gas sensor is two or more of the gas sensors.

8. The gas sensor device according to claim 4,
   wherein the selection circuitry sequentially selects the at least one gas sensor from the gas sensors, and
   the measurement circuitry, whenever the at least one gas sensor is newly selected, measures the current flowing through the selected at least one gas sensor.

9. The gas sensor device according to claim 1,
   wherein the portion of the second conductive layer is allowed to come into contact with the gas.

10. The gas sensor device according to claim 1,
    wherein in each of the gas sensors, the metal oxide layer includes:
       a first metal oxide layer being in contact with the first conductive layer, a degree of oxygen deficiency of the first metal oxide layer being higher than that of the bulk region; and
       a second metal oxide layer being in contact with the second conductive layer, the second metal oxide layer including the bulk region, and
    in each of the gas sensors, the local region is in contact with the second conductive layer and passes through the second metal oxide layer.

11. The gas sensor device according to claim 1,
    wherein in each of the gas sensors, the local region is present right under the exposed portion of the second conductive layer.

12. The gas sensor device according to claim 1,
    wherein in each of the gas sensors, the second conductive layer dissociates the hydrogen atom from a molecule contained in the gas.

13. The gas sensor device according to claim 1,
    wherein the gas sensors are each reversely changed between a high resistive state and a low resistive state in accordance with a voltage applied between the first conductive layer and the second conductive layer.

14. The gas sensor device according to claim 1, further comprising:
    first wires extending in a first direction;
    second wires extending in the first direction; and
    third wires extending in a second direction not in parallel to the first direction,
    wherein the transistors each include:
       a first terminal connected to a corresponding one of the first wires;
       a second terminal connected to a corresponding one of the gas sensors; and
       a control terminal connected to a corresponding one of the third wires, and
    the gas sensors each include:
       a first terminal connected to a corresponding one of the transistors; and a second terminal connected to a corresponding one of the second wires.

15. The gas sensor device according to claim 1, further comprising:
   first wires extending in a first direction;
   second wires extending in a second direction not in parallel to the first direction; and
   third wires extending in the first direction,
   wherein the transistors each include:
      a first terminal connected to a corresponding one of the first wires;
      a second terminal connected to a corresponding one of the gas sensors; and
      a control terminal connected to a corresponding one of the third wires, and
   the gas sensors each include:
      a first terminal connected to a corresponding one of the transistors; and
      a second terminal connected to a corresponding one of the second wires.

16. A gas sensor module comprising:
   the gas sensor device according to claim 1; and
   a wireless communication device that communicates with a searching module,
   wherein the gas sensor device receives a predetermined signal from the searching module through the wireless communication device and performs sensing of the gas based on the predetermined signal.

17. A gas detection method using a gas sensor device, wherein the gas sensor device comprises:
   gas sensors; and
   switches connected to the respective gas sensors in series,
   the gas sensors each include:
      a first conductive layer;
      a second conductive layer;
      a metal oxide layer which is disposed between the first conductive layer and the second conductive layer, the metal oxide layer including a bulk region and a local region surrounded by the bulk region, a degree of oxygen deficiency of the local region being higher than that of the bulk region; and
      an insulation layer covering the first conductive layer, the second conductive layer, and the metal oxide layer, the insulation layer having an opening from which a portion of the second conductive layer is exposed,
   the gas detection method comprising:
      selecting at least one gas sensor from the gas sensors by turning on at least one of the switches, and
      detecting a gas containing a hydrogen atom by detecting a decrease in resistance of the selected at least one gas sensor,
   wherein the switches are transistors,
   the transistors are disposed on a common substrate, and
   the gas sensors are disposed on the respective transistors.

18. The gas detection method according to claim 17, wherein in the selecting, the at least one gas sensor is sequentially selected, and
   the detecting is performed whenever the at least one gas sensor is newly selected.

* * * * *